United States Patent
Kuroki et al.

(12) 
(10) Patent No.: US 11,846,615 B2
(45) Date of Patent: Dec. 19, 2023

(54) DATA STRUCTURE AND COMPOSITE DATA GENERATION DEVICE

(71) Applicant: AROMA BIT, INC., Tokyo (JP)

(72) Inventors: Shunichiro Kuroki, Tokyo (JP); Kenichi Hashizume, Tokyo (JP); Megumi Takahashi, Tokyo (JP); Erika Terada, Tokyo (JP); Makoto Yoshimura, Tokyo (JP)

(73) Assignee: AROMA BIT, INC., Tokyo (JP)

( * ) Notice: Subject to any disclaimer, the term of this patent is extended or adjusted under 35 U.S.C. 154(b) by 475 days.

(21) Appl. No.: 16/719,421

(22) Filed: Dec. 18, 2019

(65) Prior Publication Data
US 2020/0124577 A1 Apr. 23, 2020

Related U.S. Application Data

(63) Continuation of application No. PCT/JP2017/022600, filed on Jun. 19, 2017.

(51) Int. Cl.
*G01N 30/00* (2006.01)
*G01N 30/86* (2006.01)
(Continued)

(52) U.S. Cl.
CPC ........ *G01N 30/8651* (2013.01); *G01N 30/64* (2013.01); *G01N 33/0036* (2013.01);
(Continued)

(58) Field of Classification Search
CPC .................................................. G01N 30/00
See application file for complete search history.

(56) References Cited

U.S. PATENT DOCUMENTS

| | | | | |
|---|---|---|---|---|
| 2,837,912 A | * | 6/1958 | Moncrieff | G01N 33/0001 73/865.7 |
| 4,614,299 A | * | 9/1986 | Van Loveren | A01M 1/2055 239/6 |

(Continued)

FOREIGN PATENT DOCUMENTS

| | | |
|---|---|---|
| CN | 103308650 A | 9/2013 |
| JP | H06108509 | * 4/1994 |

(Continued)

OTHER PUBLICATIONS

WIPO translation of international search report for WO2017085939, dated 2017 (Year: 2017).*
(Continued)

*Primary Examiner* — Jamel E Williams
*Assistant Examiner* — Alex T Devito
(74) *Attorney, Agent, or Firm* — FRESH IP PLC; Clifford D. Hyra; Aubrey Y. Chen

(57) ABSTRACT

A data structure includes a main data storage area in which main data is stored, and an odor data storage area in which odor data is stored. The odor data is based on a measurement result of an odor in air measured by an odor sensor. The odor data storage area stores a plurality of pieces of the odor data. The main data storage area includes a main data ID area for storing a main data ID indicating that the stored data is the main data. The odor data storage area includes an odor data ID area for storing an odor data ID indicating that the stored data is the odor data.

20 Claims, 24 Drawing Sheets

(51) Int. Cl.
  *G01N 30/64* (2006.01)
  *G01N 33/00* (2006.01)
  *G01N 30/02* (2006.01)

(52) U.S. Cl.
  CPC ......... *G01N 33/0062* (2013.01); *G01N 30/00* (2013.01); *G01N 2030/025* (2013.01)

(56) References Cited

U.S. PATENT DOCUMENTS

| | | |
|---|---|---|
| 2007/0106721 A1 | 5/2007 | Schloter |
| 2013/0244336 A1 | 9/2013 | Mayer |
| 2014/0096590 A1 | 4/2014 | Amin |
| 2018/0266977 A1 | 9/2018 | Hashizume |

FOREIGN PATENT DOCUMENTS

| | | | |
|---|---|---|---|
| JP | 11-264808 | * | 9/1999 |
| JP | 2004142994 | * | 5/2004 |
| JP | 2011507083 A | | 3/2011 |
| JP | 2014085114 A | | 5/2014 |
| JP | 2016186426 A | | 10/2016 |
| JP | WO2017/085796 A1 | | 5/2017 |
| KR | 20110043838 | * | 4/2011 |
| WO | 2016031080 A1 | | 3/2016 |
| WO | 2017085796 A1 | | 5/2017 |

OTHER PUBLICATIONS

International Search Report dated Aug. 29, 2017.
Extended European Search Report for European Application EP17914857A, dated Mar. 1, 2021.
Translation of Japanese Office Action for Japanese patent application 2019-524734, dated Jun. 22, 2021.
Office Action issued by Japanese Patent Office dated Sep. 13, 2022 for Japanese Patent Application No. 2021-176837.
Notice of First Review Opinion for CN Application No. 201780091545.X, dated Jan. 5, 2022.
Office Action for CN Application No. 201780091545.X, dated Jul. 19, 2023.

* cited by examiner

FIG.3
D1

| TIME t [SECOND] | SENSOR ELEMENTS | | | | | | |
|---|---|---|---|---|---|---|---|
| | 11-01 | 11-02 | 11-03 | 11-04 | 11-05 | ... | 11-35 |
| 0 | 16101528 | 16081740 | 16046626 | 16052233 | 16054281 | | 16043665 |
| 1 | 16101527 | 16081740 | 16046624 | 16052233 | 16054275 | | 16043667 |
| 2 | 16101529 | 16081743 | 16046626 | 16052233 | 16054279 | | 16043670 |
| 3 | 16101529 | 16081740 | 16046626 | 16052233 | 16054278 | | 16043667 |
| 4 | 16101530 | 16081741 | 16046626 | 16052234 | 16054279 | | 16043666 |
| 5 | 16101533 | 16081744 | 16046625 | 16052238 | 16054281 | | 16043674 |
| 6 | 16101531 | 16081741 | 16046627 | 16052239 | 16054283 | | 16043663 |
| 7 | 16101530 | 16081739 | 16046626 | 16052234 | 16054282 | | 16043668 |
| 8 | 16101530 | 16081740 | 16046626 | 16052233 | 16054277 | | 16043664 |
| 9 | 16101530 | 16081740 | 16046625 | 16052234 | 16054275 | | 16043676 |
| 10 | 16101528 | 16081740 | 16046625 | 16052234 | 16054281 | | 16043665 |
| 11 | 16101530 | 16081741 | 16046626 | 16052234 | 16054278 | | 16043669 |
| 12 | 16101531 | 16081741 | 16046626 | 16052234 | 16054278 | | 16043670 |
| 13 | 16101532 | 16081742 | 16046626 | 16052238 | 16054281 | | 16043666 |
| 14 | 16101537 | 16081751 | 16046629 | 16052241 | 16054287 | | 16043665 |
| 15 | 16101528 | 16081745 | 16046628 | 16052235 | 16054273 | | 16043667 |
| 16 | 16101517 | 16081728 | 16046619 | 16052226 | 16054271 | | 16043667 |
| 17 | 16101515 | 16081732 | 16046622 | 16052223 | 16054273 | | 16043665 |
| 18 | 16101517 | 16081744 | 16046623 | 16052225 | 16054276 | | 16043667 |
| 19 | 16101522 | 16081736 | 16046622 | 16052232 | 16054277 | | 16043668 |
| 20 | 16101531 | 16081738 | 16046622 | 16052239 | 16054277 | ... | 16043665 |
| 21 | 16101523 | 16081734 | 16046626 | 16052228 | 16054280 | | 16043667 |
| 22 | 16101529 | 16081737 | 16046623 | 16052232 | 16054274 | | 16043662 |
| 23 | 16101528 | 16081737 | 16046624 | 16052233 | 16054277 | | 16043667 |
| 24 | 16101518 | 16081734 | 16046624 | 16052223 | 16054270 | | 16043664 |
| 25 | 16101523 | 16081731 | 16046623 | 16052223 | 16054270 | | 16043665 |
| 26 | 16101519 | 16081731 | 16046622 | 16052223 | 16054270 | | 16043668 |
| 27 | 16101521 | 16081731 | 16046624 | 16052225 | 16054270 | | 16043670 |
| 28 | 16101525 | 16081735 | 16046625 | 16052229 | 16054280 | | 16043667 |
| 29 | 16101527 | 16081735 | 16046624 | 16052229 | 16054271 | | 16043667 |
| 30 | 16101519 | 16081732 | 16046623 | 16052223 | 16054269 | | 16043666 |
| 31 | 16101519 | 16081734 | 16046624 | 16052226 | 16054275 | | 16043668 |
| 32 | 16101529 | 16081734 | 16046626 | 16052234 | 16054274 | | 16043667 |
| 33 | 16101519 | 16081732 | 16046623 | 16052223 | 16054273 | | 16043668 |
| 34 | 16101520 | 16081730 | 16046622 | 16052221 | 16054269 | | 16043667 |
| 35 | 16101523 | 16081732 | 16046623 | 16052226 | 16054269 | | 16043667 |
| 36 | 16101521 | 16081734 | 16046624 | 16052226 | 16054272 | | 16043667 |
| 37 | 16101524 | 16081733 | 16046624 | 16052229 | 16054275 | | 16043665 |
| 38 | 16101522 | 16081733 | 16046624 | 16052227 | 16054278 | | 16043664 |
| 39 | 16101523 | 16081734 | 16046624 | 16052229 | 16054273 | | 16043664 |
| 40 | 16101517 | 16081735 | 16046623 | 16052226 | 16054274 | | 16043666 |

FIG.4

| TIME t [SECOND] | SENSOR ELEMENTS | | | | | | |
|---|---|---|---|---|---|---|---|
| | 11-01 | 11-02 | 11-03 | 11-04 | 11-05 | ... | 11-35 |
| 0 | 0 | 0 | 0 | 0 | 0 | | 0 |
| 1 | -1 | 0 | -2 | 0 | -6 | | 2 |
| 2 | 1 | 3 | 0 | 0 | -2 | | 5 |
| 3 | 1 | 0 | 0 | 0 | -3 | | 2 |
| 4 | 2 | 1 | 0 | 1 | -2 | | 1 |
| 5 | 5 | 4 | -1 | 5 | 0 | | 9 |
| 6 | 3 | 1 | -1 | 6 | 2 | | -2 |
| 7 | 2 | -1 | 0 | 1 | 1 | | 3 |
| 8 | 2 | 0 | 0 | 0 | -4 | | -1 |
| 9 | 2 | 0 | -1 | 1 | -6 | | 11 |
| 10 | 0 | 0 | -1 | 1 | 0 | | 0 |
| 11 | 2 | 1 | 0 | 1 | -3 | | 4 |
| 12 | 3 | 1 | 0 | 1 | -3 | | 5 |
| 13 | 4 | 2 | 0 | 5 | 0 | | 1 |
| 14 | 9 | 11 | 3 | 8 | 6 | | 0 |
| 15 | 0 | 5 | 2 | 2 | -8 | | 2 |
| 16 | -11 | -12 | -7 | -7 | -10 | | 2 |
| 17 | -13 | -8 | -4 | -10 | -8 | | 0 |
| 18 | -11 | 4 | -3 | -8 | -5 | | 2 |
| 19 | -6 | -4 | -4 | -1 | -4 | | 3 |
| 20 | 3 | -2 | -4 | 6 | -4 | ... | -1 |
| 21 | -5 | -6 | 0 | -5 | -1 | | 2 |
| 22 | 1 | -3 | -3 | -1 | -7 | | -4 |
| 23 | 0 | -3 | -2 | 0 | -4 | | 2 |
| 24 | -10 | -6 | -2 | -10 | -11 | | -1 |
| 25 | -5 | -9 | -3 | -10 | -11 | | 0 |
| 26 | -9 | -9 | -4 | -10 | -11 | | 3 |
| 27 | -7 | -9 | -2 | -8 | -11 | | 5 |
| 28 | -3 | -5 | -1 | -4 | -1 | | 2 |
| 29 | -1 | -5 | -2 | -4 | -10 | | 2 |
| 30 | -9 | -8 | -3 | -10 | -12 | | 1 |
| 31 | -9 | -6 | -2 | -7 | -6 | | 3 |
| 32 | 1 | -6 | 0 | 1 | -7 | | 2 |
| 33 | -9 | -8 | -3 | -10 | -8 | | 3 |
| 34 | -8 | -10 | -4 | -12 | -12 | | 2 |
| 35 | -5 | -8 | -3 | -7 | -12 | | 2 |
| 36 | -7 | -6 | -2 | -7 | -9 | | 2 |
| 37 | -4 | -7 | -2 | -4 | -6 | | 0 |
| 38 | -6 | -7 | -2 | -6 | -3 | | -1 |
| 39 | -5 | -6 | -2 | -4 | -8 | | -1 |
| 40 | -11 | -5 | -3 | -7 | -7 | | 1 |

| No. | SUBJECT NAME | DATE AND TIME OF DIAGNOSIS | DIAGNOSTIC IMAGE | ODOR DATA #1 | ODOR DATA #2 | DEFINITE DIAGNOSIS | SYMPTOM / CASE | ETIOLOGY | ... |
|---|---|---|---|---|---|---|---|---|---|
| 00001 | ●●●● | 2017/1/23 12:34 | XXX_CT.xxx | 1234567890 | 2345678901 | ▲▲▲ | ××× | ○○○ | ... |
| 00002 | ○○○○ | 2017/3/21 23:45 | YYY_CT.xxx | 3456789012 | 4567890123 | — | △△△ | — | ... |
| ... | ... | ... | ... | ... | ... | ... | ... | ... | ... |

DATA STRUCTURE AND COMPOSITE DATA GENERATION DEVICE

CROSS-REFERENCE TO RELATED APPLICATION

The present application is a continuation application of International Application No. PCT/JP2017/022600, filed Jun. 19, 2017. The contents of this application are incorporated herein by reference in its entirety.

BACKGROUND

Field

The present invention relates to a data structure and a composite data generation device. Specifically, the invention relates to a data structure of odor data-containing data containing odor data and a method of generating the odor data-containing data.

Description of the Related Art

To retrieve and extract data having a specific feature from a set of various data, metadata associated with each piece of the data has been assigned to each piece of the data (see Patent Document 1: JP 2011-507083).

It is noted that there may be a strong correlation between odor and human memory. However, it has been difficult to convert odors into digital data. For this reason, for example, even though there is a potential demand, it has been considered difficult to realize retrieving or extracting a set of data such as a digital image based on odor.

The invention has been conceived in view of the above-mentioned circumstances, and it is an illustrative problem to provide a data structure and a composite data generation device allowing search and extraction of data associated with specific odor data from a data set.

SUMMARY

To solve the above-mentioned problem, the invention has the following configuration.

(1) A data structure including a main data storage area in which main data is stored, and an odor data storage area in which odor data based on a measurement result of an odor in an air measured by an odor sensor is stored.

Further objects and other features of the invention will become apparent from a preferred embodiment described below with reference to accompanying drawings.

According to the invention, it is possible to provide a data structure and a composite data generation device allowing search and extraction of data associated with specific odor data from a data set.

BRIEF DESCRIPTION OF THE DRAWINGS

FIG. 3 is a measurement result database D1;

FIG. 4 is a processed database D2;

FIG. 6 is an explanatory diagram illustrating a processing example of an odor measurement result;

FIG. 15 is a database D11 of Example 1;

DETAILED DESCRIPTION

First Embodiment

Hereinafter, a data structure according to a first embodiment will be described with reference to drawings. The "odor" can be acquired by a human or living things including the human as olfactory information and corresponds to a concept including a molecular simple substance or a group of molecules made of different molecules gathered with respective concentrations.

In Embodiment 1, the molecular simple substance or the group of molecules made of different molecules gathered with respective concentrations included in the odor is referred to as an "odor substance". However, in a broad sense, the odor substance may broadly mean a substance which can be adsorbed on a substance adsorbing membrane of an odor sensor 10, which will be described below. That is, since the "odor" contains a plurality of odor substances responsible for the odor in many cases, and a substance not recognized as the odor substance or an unknown odor substance may be present, a substance generally not regarded as an odor causing substance may be contained.

Figure 1:
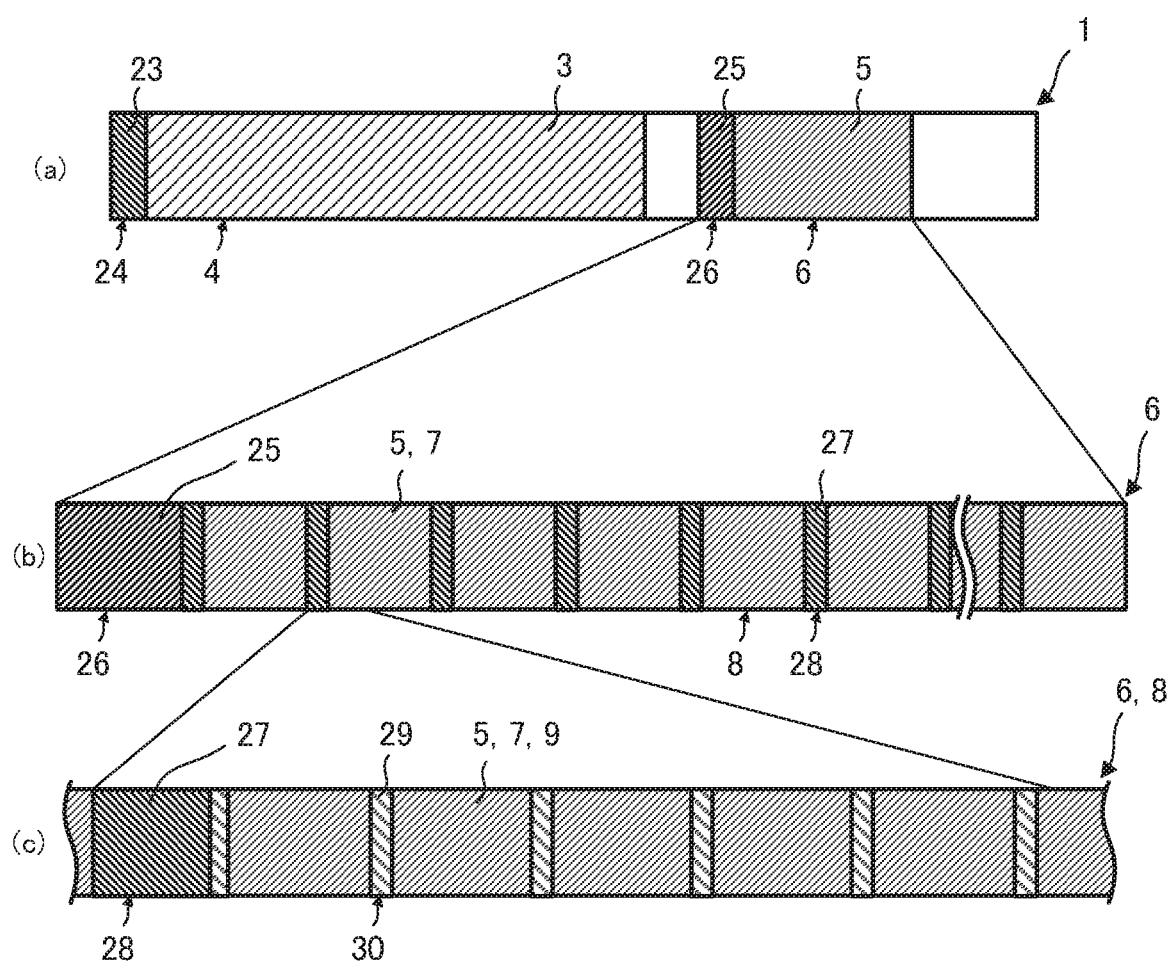
FIG. 1 is an explanatory diagram illustrating a first example of a data structure according to a first embodiment.

FIG. 1 is an explanatory diagram illustrating a first example of the data structure according to the first embodiment. As illustrated in FIG. 1(*a*), an odor data-containing data 1 having the data structure according to the first embodiment includes a main data storage area 4 and an odor data storage area 6. That is, the data structure according to the first embodiment is a data structure in which main data 3 stored in the main data storage area 4 is stored in association with odor data 5 stored in the odor data storage area 6. The data structure according to the first embodiment is a data structure for odor data that allows, for example, analysis of the main data 3 based on the odor data 5.

The main data 3 such as image data, location data, movie data, etc. associated with the odor data 5 are stored in the main data storage area 4. The odor data 5 associated with the main data 3 is stored in the odor data storage area 6. That is, the main data 3 and the odor data 5 are present in the odor data-containing data 1 in a state of being associated with each other. In the first embodiment, all the odor data-containing data 1, the main data 3 and the odor data 5 are electronic data and information to be processed by a computer, etc.

As the main data 3, various data can be used as the main data 3 without particular limitation. For example, it is possible to use, as the main data 3, various data such as image data generated by an imaging device, movie data generated by a video recording device, audio data generated by an audio recording device, text data such as sentences, location data generated by a GPS device, etc.

The main data storage area 4 may have a main data ID area 24. The main data ID area 24 is an area for storing a main data ID 23. The main data ID 23 is data indicating that data stored in the main data storage area 4 is the main data 3.

As the odor data 5, for example, it is possible to use data generated based on a measurement result measured by an odor measurement apparatus 50 including the odor sensor 10 described later. As the odor sensor 10, it is possible to use a sensor including a plurality of sensor elements 11. Each of the sensor elements 11 includes a substance adsorbing membrane 13 and a detector 15. The substance adsorbing membrane 13 adsorbs an odor substance in the air. The detector 15 detects an adsorption state in which the odor substance is adsorbed to the substance adsorbing membrane 13. The respective sensor elements 11 have different substance adsorbing membranes 13. That is, an adsorption characteristic of the odor substance on the substance adsorbing membrane 13 is different in each sensor element 11.

The odor data storage area 6 may have an odor data ID area 26. The odor data ID area 26 is an area for storing an odor data ID 25. The odor data ID 25 is data indicating that data stored in the odor data storage area 6 is the odor data 5.

In the odor data storage area 6, a single piece of odor data 5 may be stored or a plurality of pieces of odor data 5 may be stored. When the plurality of pieces of odor data 5 are stored in the odor data storage area 6, each of the plurality of pieces of odor data 5 may correspond to each of the plurality of sensor elements 11 included in the odor sensor 10 on a one-to-one basis. In the following description, each piece of odor data 5 corresponding to each of the plurality of sensor elements 11 may be referred to as element data 7. In the odor data storage area 6, each of a plurality of pieces of element data 7 may be stored in an element data storage area 8 as illustrated in FIG. 1(b).

A plurality of odor data ID areas 26 may be included in the odor data storage area 6. The plurality of odor data ID areas 26 can be associated with each of the plurality of pieces of odor data 5 stored in the odor data storage area 6 on a one-to-one basis. In the following description, when the plurality of odor data ID areas 26 is present, each of the odor data ID areas 26 may be referred to as an element data ID area 28. An element data ID 27 is stored in each element data ID area 28. The element data ID 27 is data indicating, for example, that data stored in the element data ID area 28 is data corresponding to a specific sensor element 11. Each element data ID area 28 corresponds to each of the plurality of sensor elements 11 included in the odor sensor 10 on a one-to-one basis.

The respective element data storage areas 8 are preferably arranged in alignment in the odor data storage area 6. When numbers are assigned to the sensor elements, it is preferable that the element data storage areas 8 corresponding to the sensor elements of the numbers are aligned in the odor data storage area 6 in the order of assigned number.

The odor data 5 may be a measurement result measured by the sensor element 11 of the odor sensor 10. That is, the odor data 5 may be raw data used without processing the measurement result of the odor sensor 10. Specifically, a measurement result of odor in the air measured by the odor sensor 10 may be transitional data indicating a temporal change of the odor in the air.

The transitional data may be measured by the odor sensor 10 at predetermined time intervals over a predetermined time width. The transitional data may be configured to have a plurality of data sets including a measurement value obtained by measuring the odor in the air by the odor sensor 10 and a measurement time of the measurement value.

For example, as illustrated in FIG. 1(c), the odor data 5 (transitional data) may be data including a plurality of element data points 9 (measurement values) at each time (tx) measured at each of the sensor elements 11 with the lapse of time from a measurement start time (t0) to a measurement end time (tz). Data at a measurement time is associated with each element data point 9 (measurement value) on a one-to-one basis, and the odor data 5 (transitional data) includes a plurality of data sets having the element data points 9 and the measurement times. In this specification, the time (tx), a time (ty) and the time (tz) are arbitrary times after x seconds, y seconds and z seconds from the measurement start time (t0), respectively.

The odor data 5 may include an element data point 9 at the measurement start time (t0), an element data point 9 at the time (tx) after a predetermined time (x) has elapsed from the measurement start time (t0), and an element data point 9 at the measurement end time (tz). It is preferable that the respective element data points 9 are aligned in the odor data storage area 6 in the order of measurement time. It is preferable that a plurality of element data points 9 at the time (tx) is provided. For example, when element data points 9 are acquired at one second intervals from the measurement start time (t0) to the measurement end time (t40) after 40 seconds, 39 element data point 9 at the time (tx) are obtained from x=1 to x=39.

As illustrated in FIG. 1(c), the element data storage area 8 may have a time label area 30 for storing a time label 29 corresponding to each element data point 9. That is, a time label area 30 for storing a time label 29 which indicates a time (tx) at which each element data point 9 is measured may be arranged in the element data storage area 8. The time label area 30 is preferably arranged in the order of passage of time in the element data storage area 8. However, since the time label 29 is assigned, each element data point 9 may be randomly arranged regardless of the order of passage of time.

As the element data 7, instead of the raw data, it is possible to use processed data arithmetically processed by an arithmetic processing device (CPU) 51 included in the odor sensor 10. For example, a set of element data points 9 at each measurement time (tx) in raw data can be arithmetically processed based on a predetermined rule. As arithmetic processing, it is possible to detect a maximum value and a minimum value from a set of element data points 9, calculate a difference thereof (absolute value), and use the value as the element data 7. In addition, as arithmetic processing, it is possible to calculate an average value such as an arithmetic mean value, a median value, etc. from a set of element data points 9, and use the value as the element data 7. When processed data is used as the element data 7, basically one piece of data corresponding to each sensor element 11 is sufficient. Thus, it is possible to efficiently store a large amount of information in the odor data storage area 6 without causing data enlargement.

Figure 2:
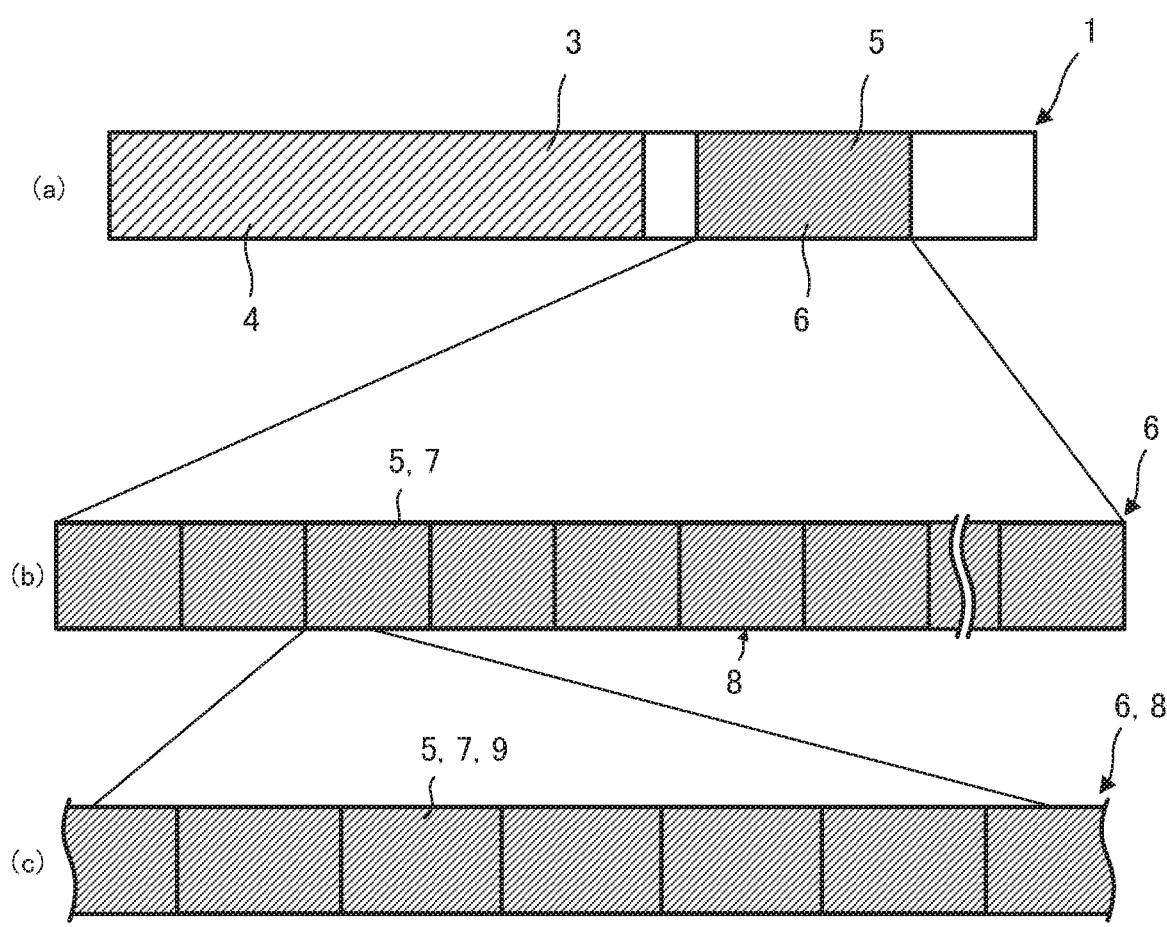
FIG. 2 is an explanatory diagram illustrating a second example of the data structure according to the first embodiment.

FIG. 2 is an explanatory diagram of a second example of the data structure according to the first embodiment. As illustrated in FIGS. 2(a) to 2(c), the data structure according to the first embodiment may be set as a structure not having the main data ID area 24, the odor data ID area 26, the element data ID area 28, and the time label area 30. In this case, the main data 3 and the odor data 5 may be stored in the main data storage area 4 and the odor data storage area 6, respectively, determined in advance as predetermined areas of the odor data-containing data 1.

Respective pieces of the element data 7 can be aligned and stored in the odor data storage area 6 in a predetermined order. When numbers are assigned to the respective sensor elements 11, the respective pieces of the element data 7 can be stored in the order of number. In addition, in a case in which numbers are assigned to the respective sensor elements 11, when the order of alignment in the odor data storage area 6 and the numbers of the corresponding sensor elements 11 are correlated and stored in a storage device 53 and the like, the respective pieces of the element data 7 may not be aligned in the order of the sensor elements 11. The respective element data points 9 can be aligned and stored in chronological order of measurement.

Two examples have been shown using FIG. 1 (first example) and FIG. 2 (second example) with regard to the data structure according to the first embodiment. However, the data structure is not limited thereto. In the first example, it is possible to adopt a data structure not having at least one of the main data ID area 24, the odor data ID area 26, the element data ID area 28, and the time label area 30. In addition, in the second example, it is possible to adopt a data structure having at least one of the main data ID area 24, the odor data ID area 26, the element data ID area 28, and the time label area 30.

Next, a process of odor acquisition by the odor sensor 10 will be described. The odor acquisition by the odor sensor 10 can be realized by respective steps of a measurement result acquisition step S1 and a data processing step S2.

<Measurement Result Acquiring Step S1>

In a measurement result acquiring step S1, each measurement result measured with respect to an odor substance included in a sample by each of plurality of sensor elements 11 included in the odor sensor 10 is acquired by using the odor sensor 10. Each of the plurality of sensor elements 11 has different detection properties with respect to the odor substance. A specific configuration of the odor sensor 10 will be described below.

Each of the measurement results is acquired associated with each of the plurality of sensor elements 11. Specifically, the measurement result can be acquired as a measurement result database in which the measurement result is stored in a state where each of the sensor elements 11 and each of the measurement results measured in each of the sensor elements 11 are associated with each other.

FIG. 3 is a measurement result database D1. In the measurement result database D1, the measurement result is stored in a state where each of the sensor elements 11 and each of the measurement results measured in each of the sensor elements 11 are associated with each other. In the measurement result database D1 illustrated in FIG. 1, the measurement result is stored in a state where the measurement results are respectively associated with a total of 35 sensor elements 11 of sensor elements 11-01 to 11-35. Incidentally, in FIG. 1, for the convenience of the description, the description of the sensor elements 11-06 to 11-34 is omitted. The measurement result database D1 illustrated in FIG. 3 shows measurement results (data points 9) when the odor sensor 10 is brought into contact with an odor to be measured during a time t of 15 seconds to 20 seconds.

Specifically, the measurement result is raw data which is detected by each of the sensor elements 11. In a case where the odor sensor 10, for example, is a quartz oscillator sensor (QCM), a temporal change in a resonance frequency of a quartz oscillator can be the raw data that is generated by the sensor element 11. That is, a resonance frequency at a plurality of time points (data points 9) having different elapse times from an operation start of the odor sensor 10 can be the measurement result according to the sensor element 11. For example, as illustrated in FIG. 3, as the measurement result measured in the sensor element 11-01 (data point 9), a resonance frequency measured after 0 second (t0) is "16101528 Hz", and a resonance frequency measured after 17 seconds (t17) is "16101515 Hz". In addition, as the measurement result measured in the sensor element 11-02 (data point 9), a resonance frequency measured after 0 second (t0) from the operation start of the odor sensor 10 is "16081740 Hz", and a resonance frequency measured after 16 seconds (t16) from the operation start of the odor sensor 10 is "16081728 Hz". Incidentally, in the measurement, a time interval of recording the measurement result is not particularly limited and can be an interval of 1 second for example.

A time width from a start to an end of an operation of the odor sensor 10 is not particularly limited. However, it is preferable that the time width is longer than a time width for bringing the odor sensor 10 into contact with the odor to be measured. In addition, the start of the operation of the odor sensor 10 is preferably several seconds or more, preferably 5 seconds or faster before the odor sensor 10 is brought into contact with the odor to be measured (odor measurement). The end of the operation of the odor sensor 10 is preferably several seconds or more, preferably 5 seconds or later after the odor sensor 10 is brought into contact with the odor to be measured. In the measurement result database D1 illustrated in FIG. 3, the operation start of the odor sensor 10 is 15 seconds (t0) before the start of the odor measurement, and the operation end of the odor sensor 10 is 20 seconds (t40) after the end of the odor measurement.

It is preferable that the measurement of the odor sensor 10 is performed a plurality of times, and an average value of the raw data items of the measurement that is performed a plurality of times is acquired as the measurement result. The number of times of the measurement is not particularly limited, and for example, can be three times. An average value according to an arithmetic average (an arithmetic means) can be adopted as the average value.

<Data Processing Step S2>

In the data processing step S2, each of the measurement results acquired in the measurement result acquisition step S1 is processed to generate the odor data 5 (processed data) associated with each of the plurality of sensor elements 11.

As the processed data, it is possible to use the average value or the median value of the measurement results of the odor in the air measured by the odor sensor 10 in a predetermined time width. The processed data is not limited thereto, and may be the processed data described below.

(Difference Data Based on t0)

The odor data 5 may be difference data between a first measurement result of the odor in the air at a first time or time width for indicating a temporal change of the odor in the air and a second first measurement result of the odor in the air at a second time or time width, which is the measurement result of the odor in the air measured by the odor sensor 10. For example, the odor data 5 may be, as processed data, a difference between a data point 9 at a predetermined time (tx) and a data point 9 at a predetermined time (ty).

FIG. 4 is a processed database D2. As illustrated in FIG. 4, the odor data 5 may subtract a value at a time 0 (t0) from each measurement result in a time width (t1 to t40) after the time 0 as difference data. That is, the odor data 5 may be difference data based on the measurement result at the time 0 (t0).

(Difference Data Between Two Different Points)

As the difference data, it is possible to use difference data between a first measurement result which is a measurement result of the odor in the air at the first time and a second measurement result which is a measurement result of the odor in the air at the second time. In this instance, a time difference between the first time and the second time is preferably at least several seconds, more preferably at least 5 seconds, and particularly preferably at least 10 seconds. For example, when the difference data is acquired between two points at an interval of several seconds or more between a time when the odor substance to be measured is in contact with the odor sensor 10 and a time when the odor substance is not in contact, the characteristic of the odor can be made clearer as the odor data 5.

As such difference data between two different points, for example, it is possible to use a difference between a measurement result (data point 9) at each time and a measurement result (data point 9) at the time 0 (t0).

As difference data between two different points, for example, it is possible to use a difference (absolute value) between a maximum value of measurement results in a predetermined time width and a minimum value of measurement results in a predetermined time width. Here, the predetermined time width including the maximum value and the predetermined time width including the minimum value may or may not overlap. In the case of overlapping, a part or a whole may overlap. As the predetermined time width, it is possible to use a time width for odor measurement, or a time width (time width for background measurement) other than the time width for odor measurement. Specifically, a difference between a maximum value among the measurement results in the odor measurement time width and a minimum value in the time width (background) other than the odor measurement time width can be used as difference data. A difference between a maximum value among the measurement results in the odor measurement time width and a minimum value in the odor measurement time width can be used as difference data. A difference between a minimum value among the measurement results in the odor measurement time width and a maximum value in the time width (background) other than the odor measurement time width can be used as difference data. A difference between a minimum value among the measurement results in the odor measurement time width and a maximum value in the odor measurement time width can be used as difference data.

As the difference data, it is possible to use a difference (absolute value) between a maximum value or a minimum value among measurement results in a predetermined time width and an average value or a median value of the measurement results in the predetermined time width.

As the difference data, in a case in which control devices 55, 57, and 59, etc. are arranged in the odor measurement apparatus 50 as described below, when air containing the odor substance of the odor to be measured is introduced from an introduction port 56, a difference between a measurement result in a state in which the control device 55 is open and a measurement result in a state in which the control device 55 is closed can be used as the difference data. The control devices 55, 57, and 59 may be fans, shutters, seal valves, etc. When the control device 55 is a fan, a difference between a measurement result in a state in which the fan is rotating (forward rotation) in a direction introducing air containing the odor substance to be measured and a measurement result in a state in which the fan is stopped or rotating in the opposite direction (reverse) can be used as the difference data.

As the difference data, it is possible to use a difference between a maximal value and a first minimal value after the maximal value (hereinafter, also referred to as a "minimal value immediately after the maximal value") for a measurement result (raw data) acquired in the measurement result acquisition step S1. In a case where there are a plurality of such differences (between the maximal value and the minimal value immediately after the maximal value), the difference (absolute value) having the largest value is adopted as the difference of the measurement result. In such a manner, the difference associated with each of the plurality of sensor elements 11 is obtained for each of the measurement results.

Figure 5:
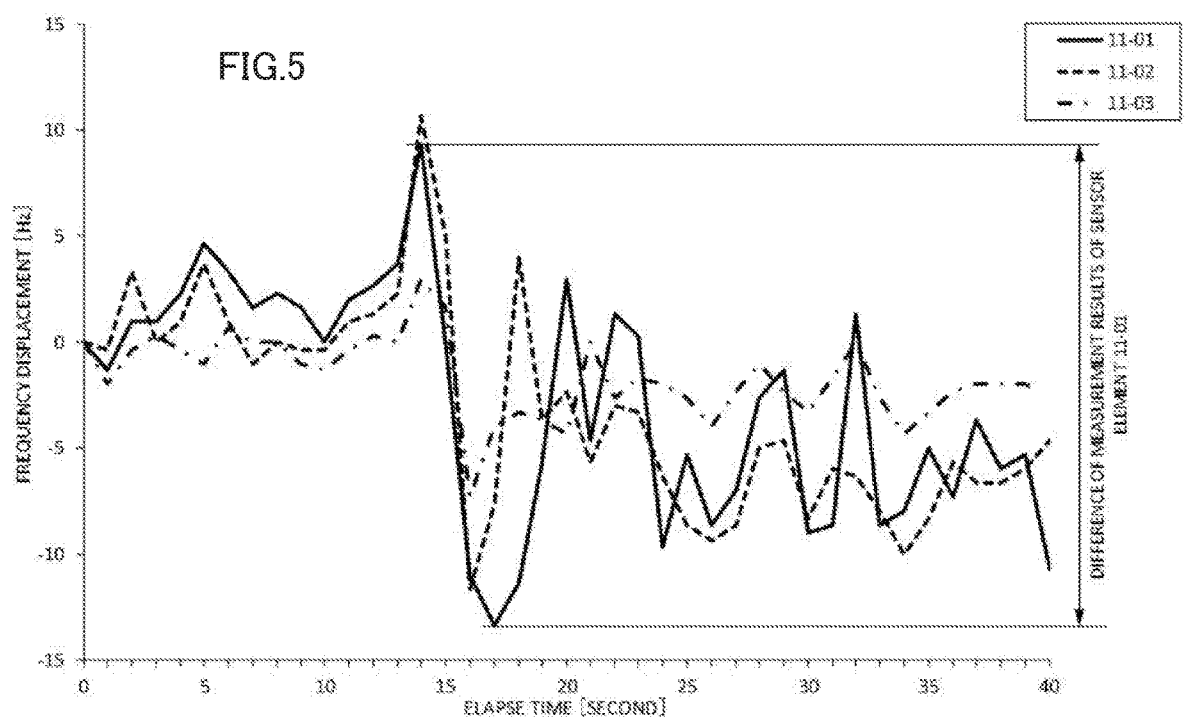
FIG. 5 is a graph illustrating a measurement result based on the processed database D2.

FIG. 5 is graph illustrating a measurement result based on the processed database D2. In the graph of FIG. 5, a difference between a local maximum and a local minimum immediately after the local maximum is used as difference data. In FIG. 5, the vertical axis denotes a displacement amount [Hz] of a resonance frequency which is measured after a predetermined time, on the basis of the resonance frequency after 0 seconds from the operation start of the odor sensor 10, and the horizontal axis denotes an elapse time [second] from the operation start of the odor sensor 10. In FIG. 5, among the measurement results represented in the processed database D2, the measurement results of the sensor elements 11-01, 11-02, and 11-03 are illustrated. In FIG. 5, the measurement result of the sensor element 11-01 is represented by a solid line, the measurement result of the sensor element 11-02 is represented by a broken line, and the measurement result of the sensor element 11-03 is represented by a dashed-dotted line. It is obvious that graphs can also be prepared with respect to other sensor elements 11-04 to 11-35, similarly. In FIG. 5, in the sensor element 11-01, the difference of the measurement result is "22 Hz". That is, in the measurement result of the sensor element 11-01, the difference is the difference between the maximal value of "9 Hz" after an elapse time of 14 seconds from the operation start of the odor sensor 10, and a minimal value of "−13 Hz" after an elapse time of 17 seconds from the operation start of the odor sensor 10.

When the difference is calculated, the range of the elapse time from the operation start of the odor sensor 10 used as an odor measurement result may be limited. For example, in a case where the measurement of the odor of the sample is started after 15 seconds from the operation start of the odor sensor 10, and the measurement of the odor of the sample is ended after 20 seconds from the operation start of the odor sensor 10, the range of the elapse time for calculating the difference can be set to an elapse time of 14 seconds to 25 seconds from the operation start of the odor sensor 10. Incidentally, the range of the elapse time can be arbitrarily set.

As the processed data, a logarithmic arithmetic operation is performed with respect to each of the differences calculated, and thus, a logarithmic value associated with each of the plurality of sensor elements 11 may be used as the odor data 5 (element data 7). In the logarithmic arithmetic operation, the base is not particularly limited, and for example, can be 2.

As the processed data, it is possible to use simplified data such as data obtained by classifying measurement results and flagging the data according to the classification. For example, as described above, the logarithmic value obtained by logarithmic calculation can be classified into a plurality of areas according to a size of the value. The number of areas to be classified is not particularly limited. For example, the number may be set to three to five, etc. Hereinafter, the case of classification into three areas will be described.

First, among the logarithmic values of the respective measurement result, a maximum logarithmic value and a minimum logarithmic value are identified. Next, a quotient in a case where a difference between the maximum logarithmic value and the minimum logarithmic value is divided by 3 is calculated. A numerical range between the maximum logarithmic value and the minimum logarithmic value can be partitioned into trisected ranges by using the quotient obtained as described above. That is, the numerical range can be trisected into a range from the minimum logarithmic value to a value in which the quotient is added to the minimum logarithmic value, a range from the value in which the quotient is added to the minimum logarithmic value to a value in which twice the quotient is added to the minimum logarithmic value, and a range from the value in which twice the quotient is added to the minimum logarithmic value to the maximum logarithmic value.

Next, each of the logarithmic values associated with each of the sensor elements 11 is classified into any range of three ranges. To each of the logarithmic values, a flag for identifying the classified range may be provided. For example, for the three trisected ranges, flags such as (1), (2), and (3) in an increasing order can be provided. Accordingly, the measurement result associated with each of the sensor elements 11 can be classified into three stages in accordance with the magnitude of the value.

Figure 6:
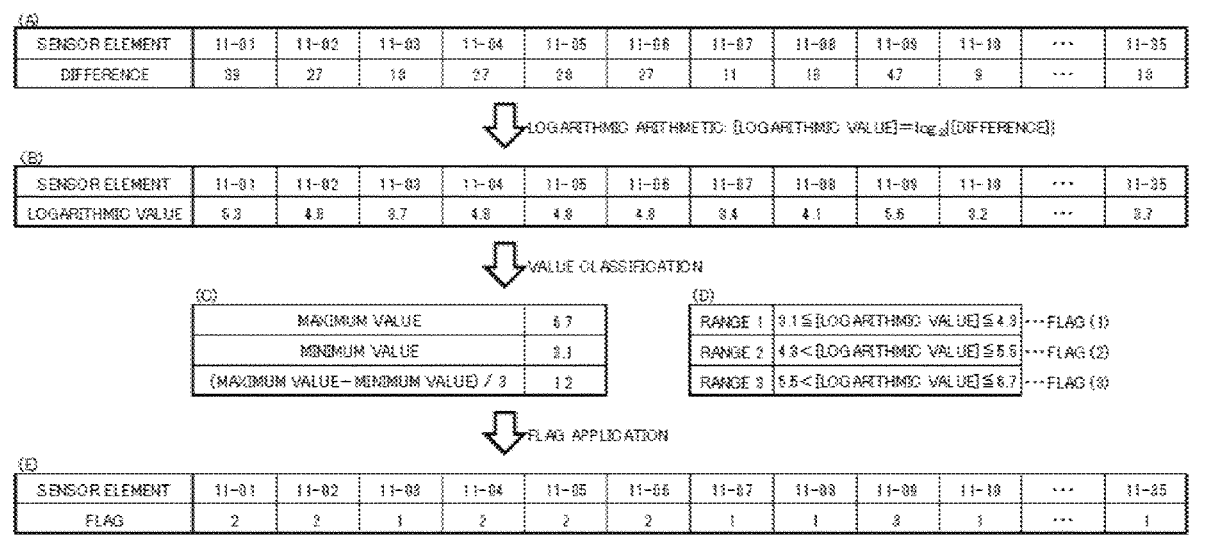

FIG. 6 is an explanatory diagram illustrating a processing example of an odor measurement result. In FIG. 6, Table (A) is a table showing the differences calculated with respect to a certain sample. The value of each of the differences of each of the sensor elements 11-01 to 11-35 is shown. For example, in Table (A), the difference obtained in the sensor element 11-01 is "38.7", and the difference obtained in the sensor element 11-02 is "27.0". Incidentally, for the convenience of the description, indication of the values of the sensor elements 11-11 to 11-34 will be omitted (the same applies to Table (B) and Table (E) described below).

Next, the differences of each of the sensor elements 11 are subjected to logarithmic arithmetic processing. Here, the logarithmic arithmetic operation is represented by Formula (1) described below. That is, an absolute value of the value of the difference is subjected to logarithmic arithmetic operation by setting the base to 2, and thus, the logarithmic value is obtained.

[Logarithmic Value]=log$_2$|[Difference]|   Formula (1)

Table (B) is a table showing the logarithmic values of each of the sensor elements 11. For example, in Table (B), the logarithmic value calculated based on the difference obtained in the sensor element 11-01 is "5.3", and the logarithmic value calculated based on the difference obtained in the sensor element 11-02 is "4.8".

Next, according to the value classifying sub-step S2-3, the logarithmic values of each of the sensor elements 11 are classified into three ranges on the basis of the obtained logarithmic value. Specifically, first, in the sample being measured, in the logarithmic values of the respective sensor elements 11, the maximum logarithmic value (maximum value) and the minimum logarithmic value (minimum value) are identified. Then, a quotient in a case where the difference between the maximum value and the minimum value is divided by 3 is calculated. The identified maximum value and minimum value, and the calculated quotient are shown in Table (C). In Table (C), the identified maximum value is "6.7", the identified minimum value is "3.1", and the calculated quotient is "1.2".

The logarithmic values of each of the sensor elements 11 are classified into three levels on the basis of the identified maximum value and minimum value, and the calculated quotient. The classification is performed on the basis of a classification rule as shown in Table (D). Specifically, the classification is performed on the basis of a classification rule in which a range of the smallest logarithmic values (range 1) is a range of 3.1≤[Logarithmic Value]≤4.3, a range of the second smallest logarithmic values (range 2) is a range of 4.3<[Logarithmic Value]≤5.5, and a range of the largest logarithmic values (range 3) is a range of 5.5<[Logarithmic Value]≤6.7.

Next, flags are applied to each of the sensor elements 11 on the basis of the classification result. The result of applying the flag to each of the sensor elements 11 is shown in Table (E). Flags (1) are applied to the sensor elements 11 in which the logarithmic value corresponding to range 1 is obtained, flags (2) are applied to the sensor elements 11 in which the logarithmic value corresponding to range 2 is obtained, and flags (3) are applied to the sensor elements 11 in which the logarithmic value corresponding to range 3 is obtained. For example, in Table (E), a flag (2) is applied to the sensor element 11-01, a flag (1) is applied to the sensor element 11-30, and a flag (3) is applied to the sensor element 11-09.

<Odor Sensor 10>

Figure 7:
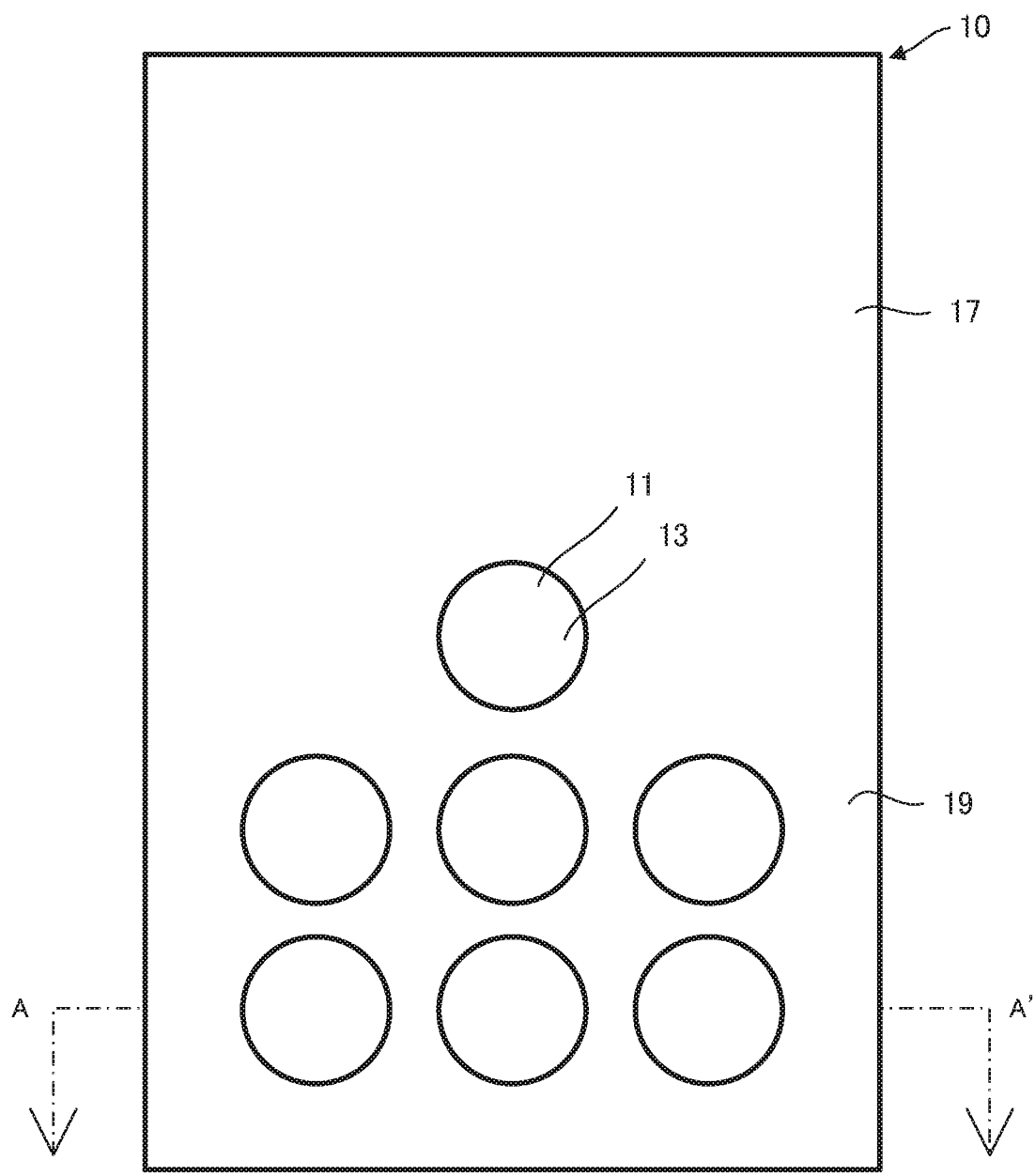
FIG. 7 is a plan view schematically illustrating a first example of an odor sensor 10 in the first embodiment.
Figure 8:
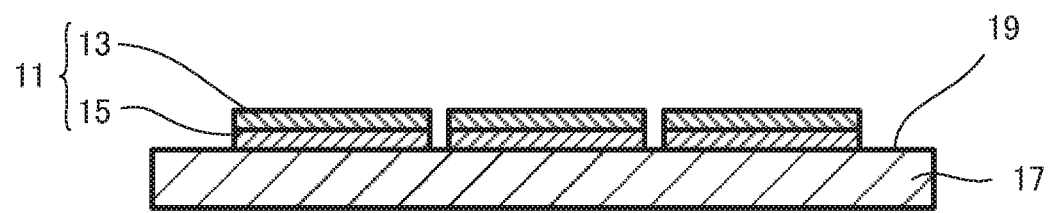
FIG. 8 is a cross-sectional view schematically illustrating a cross section A-A' in FIG. 7.

FIG. 7 is a plan view schematically illustrating a first example of the odor sensor 10 in the first embodiment. FIG. 8 is a cross-sectional view schematically illustrating the A-A' cross section of FIG. 7. The odor sensor 10 includes a plurality of sensor elements 11 and a sensor substrate 17. Each of the sensor elements 11 includes the substance adsorption membrane 13 that adsorbs the odor substance and a detector 15 that detects an adsorption state of the odor substance with respect to the substance adsorption membrane 13.

As illustrated in FIG. 8, the sensor element 11 includes the detector 15 and the substance adsorption membrane 13 provided on the surface of the detector 15. It is preferable that the substance adsorption membrane 13 covers the entire surface of the detector 15. That is, the size of the detector 15 is preferably the same as the formation range of the substance adsorption membrane 13, or smaller than the formation range of the substance adsorption membrane 13. Incidentally, a plurality of detectors 15 may be provided within the formation range of one substance adsorption membrane 13.

Figure 9:
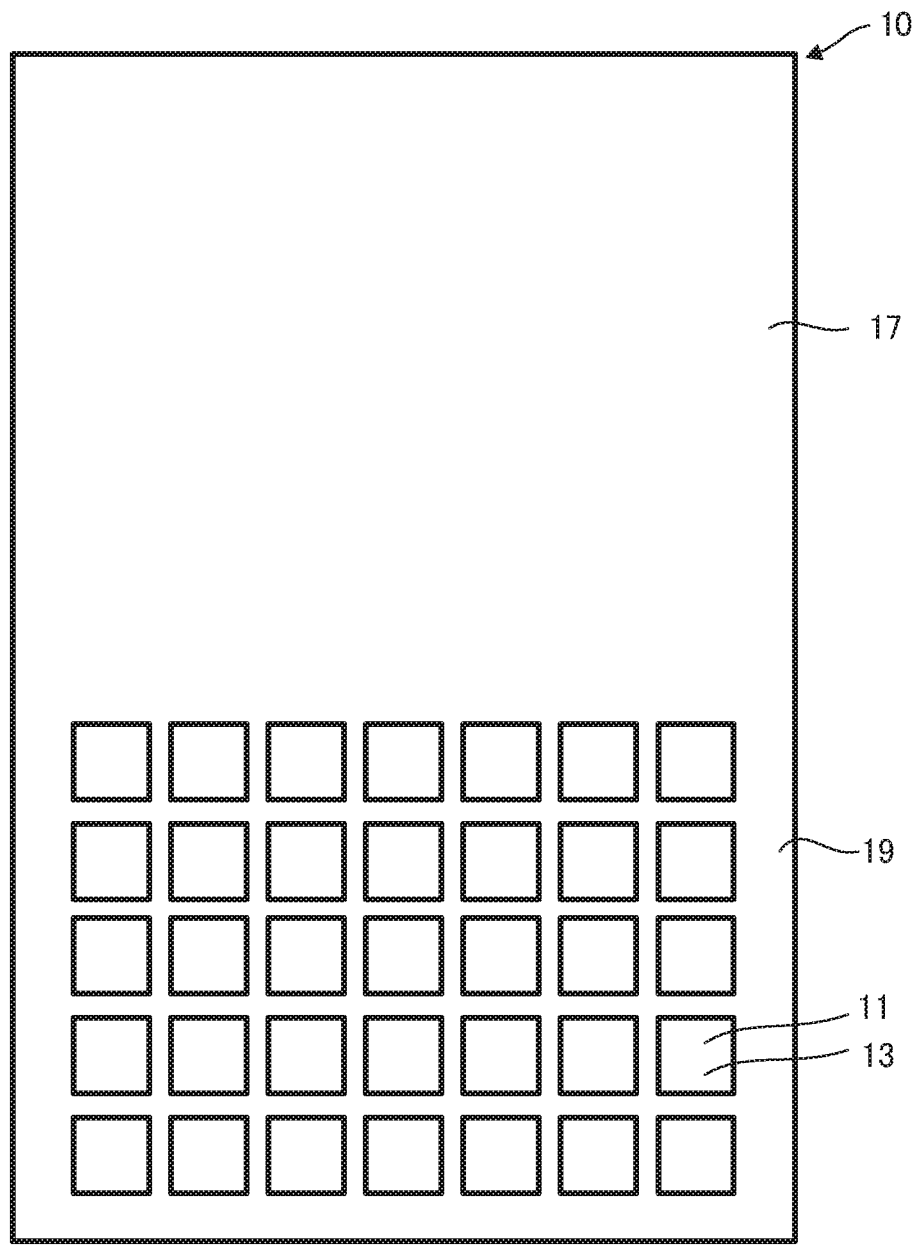
FIG. 9 is a plan view schematically illustrating a second example of the odor sensor 10 in the first embodiment.

The plurality of sensor elements 11 is arranged on a sensor substrate 17 and aligned as illustrated in FIG. 7. In this instance, substance adsorption membranes 13 of adjacent sensor elements 11 are not in contact with each other or are insulated. It should be noted that the sensor elements 11 may not be aligned on the sensor substrate 17 and may be randomly arranged or aligned in a form other than three rows and three columns. The number of sensor elements 11 on the sensor substrate 17 is not particularly limited. The number may be seven as illustrated in FIG. 7 or, for example, 35 in seven rows and five columns as illustrated in FIG. 9. FIG. 9 is a plan view schematically illustrating a second example of the odor sensor 10 in the first embodiment.

In the plurality of sensor elements 11 arranged on the sensor substrate 17, properties of the respective substance adsorption membranes 13 are different from each other. Specifically, it is preferable that all the plurality of sensor elements 11 have the substance adsorption membranes 13 of different compositions, and that substance adsorption membranes 13 of the same property do not exist. Here, the property of the substance adsorption membrane 13 can be referred to as the adsorption characteristic of the odor substance with respect to the substance adsorption membrane 13. That is, one same odor substance (or an aggregate thereof) can exhibit different adsorption properties if the substance adsorption membrane 13 has different property. In FIG. 7 to FIG. 10, for the sake of convenience, all the substance adsorption membranes 13 are illustrated in the same manner. However, in practice, properties thereof are different from each other. Incidentally, it is not necessary that the adsorption properties of all of the substance adsorbing membranes 13 of each of the sensor elements 11 are different from each other, and among them, the sensor elements 11 provided with the substance adsorbing membranes 13 having the same adsorption properties may be provided.

As a material of the substance adsorption membrane 13, it is possible to use a thin film formed of a π electron conjugated polymer. This thin film can contain at least one of an inorganic acid, an organic acid, or an ionic liquid as a dopant. By changing the type or content of the dopant, it is possible to change the property of the substance adsorption membrane 13.

Examples of the π electron conjugated polymer preferably include, but are not limited to, a polymer having the π electron conjugated polymer as a skeleton such as polypyrrole and a derivative thereof, polyaniline and a derivative thereof, polythiophene and a derivative thereof, polyacetylene and a derivative thereof, or polyazulene and a derivative thereof.

In a case in which the π electron conjugated polymer is in an oxidized state and the skeleton polymer itself is a cation, conductivity can be developed by containing an anion as a dopant. Incidentally, in the invention, a neutral π electron conjugated polymer not containing a dopant can be adopted as the substance adsorption membrane 13.

Specific examples of the dopant can include inorganic ions such as chlorine ion, chlorine oxide ion, bromine ion, sulfate ion, nitrate ion, and borate ion, organic acid anions such as alkylsulfonic acid, benzenesulfonic acid, and carboxylic acid, and polymer acid anions such as polyacrylic acid and polystyrene sulfonic acid.

In addition, it is possible to use a method of performing chemical equilibrium doping by allowing salt such as table salt or an ionic compound containing both a cation and an anion such as an ionic liquid to coexist with the neutral π electron conjugated polymer.

In a case in which a state in which one dopant unit (ion) enters per two repeating units included in the π electron conjugated polymer is set to 1, the content of the dopant in the π electron conjugated polymer may be adjusted in a range of 0.01 to 5, preferably in a range of 0.1 to 2. When the content of the dopant is set to be greater than or equal to the minimum value of this range, it is possible to inhibit disappearance of the characteristic of the substance adsorption membrane 13. In addition, when the content of the dopant is set to be less than or equal to the maximum value of this range, it is possible to inhibit a decrease in effect of the adsorption characteristic of the π electron conjugated polymer itself, which makes it difficult to produce the substance adsorption membrane 13 having a desirable adsorption characteristic. In addition, it is possible to inhibit a significant decrease in durability of the substance adsorption membrane 13 due to the dopant, which is a low molecular weight substance, when predominant in the membrane. Therefore, by setting the content of the dopant in the above-mentioned range, it is possible to suitably maintain detection sensitivity of the odor substance.

In the plurality of sensor elements 11, different types of π electron conjugated polymers can be used to vary the respective adsorption properties of the substance adsorption membranes 13. In addition, respective adsorption properties may be developed by changing the type or the content of the dopant while using the same kind of π electron conjugated polymer. For example, hydrophobic/hydrophilic properties of the substance adsorption membrane 13 can be changed by changing the type of the π electron conjugated polymer, the type and the content of the dopant, etc.

A thickness of the substance adsorption membrane 13 can be appropriately selected according to the characteristic of the odor substance to be adsorbed. For example, the thickness of the substance adsorption membrane 13 can be in a range of 10 nm to 10 μm, preferably 50 nm to 800 nm. When the thickness of the substance adsorption membrane 13 is less than 10 nm, sufficient sensitivity may not be obtained in some cases. In addition, when the thickness of the substance adsorption membrane 13 exceeds 10 μm, an upper limit of the weight detectable by the detector 15 may be exceeded.

The detector 15 has a function as a signal converter (transducer) which measures a change in physical, chemical, or electrical characteristic of the substance adsorption membrane 13 due to the odor substance adsorbed on the surface of the substance adsorption membrane 13 and outputs a measurement result thereof as, for example, an electric signal. That is, the detector 15 detects an adsorption state of the odor substance on the surface of the substance adsorption membrane 13. Examples of the signal output as the measurement result by the detector 15 include physical information such as an electric signal, light emission, a change in electric resistance, or a change in vibration frequency.

The detector 15 is not particularly limited as long as the detector 15 is a sensor which measures the change in physical, chemical, or electrical characteristic of the substance adsorption membrane 13, and various sensors can be appropriately used. Specific examples of the detector 15 include a crystal oscillator sensor (QCM), a surface elastic wave sensor, a field effect transistor (FET) sensor, a charge coupled device sensor, an MOS field effect transistor sensor, a metal oxide semiconductor sensor, an organic conductive polymer sensor, an electrochemical sensor.

Incidentally, in the case of using the crystal oscillator sensor as the detector 15, although not illustrated, as an excitation electrode, electrodes may be provided on both sides of the crystal oscillator or a separated electrode may be provided on one side to detect a high Q value. In addition, the excitation electrode may be provided on the sensor substrate 17 side of the crystal oscillator with the sensor substrate 17 interposed therebetween. The excitation electrode can be formed of an arbitrary conductive material. Specific examples of the material of the excitation electrode include inorganic materials such as gold, silver, platinum, chromium, titanium, aluminum, nickel, nickel alloy, silicon, carbon, and carbon nanotube, and organic materials such as conductive polymers such as polypyrrole and polyaniline.

As illustrated in FIG. 8, the detector 15 can have a flat-plate shape. As illustrated in FIG. 7, a shape of the flat plate of the flat-plate shape can be circular. However, the shape can be of various shapes such as a quadrangle, a square, an ellipse, etc. Further, the shape of the detector 15 is not limited to the flat plate shape. A thickness thereof may be altered, and a concave portion or a convex portion may be formed.

In a case in which the detector 15 uses an oscillator as the crystal oscillator sensor described above, it is possible to reduce the influence (crosstalk) received from another oscillator coexisting on the same sensor substrate 17 by changing resonance frequencies of respective oscillators in the plurality of sensor elements 11. It is possible to arbitrarily design the resonance frequencies so that the respective oscillators on the same sensor substrate 17 exhibit different sensitivities with respect to a certain frequency. The resonance frequency can be changed, for example, by adjusting the thickness of the oscillator or the substance adsorption membrane 13.

As the sensor substrate 17, it is possible to use a silicon substrate, a substrate made of quartz crystal, a printed wiring substrate, a ceramic substrate, a resin substrate, etc. In addition, the substrate is a multilayer wiring substrate such as an interposer substrate, and an excitation electrode for oscillating the quartz substrate, mounting wirings, and an electrode for energizing are disposed at arbitrary positions.

By adopting the configuration as described above, it is possible to obtain the odor sensor 10 including the plurality of sensor elements 11 having the substance adsorption membranes 13 whose adsorption properties of the odor substance are different from each other. As a result, in a case in which an odor of air containing a certain odor substance or a composition thereof is measured by the odor sensor 10, the odor substance or the composition thereof comes into contact with the substance adsorption membrane 13 of each sensor element 11 in the same manner. However, the odor substance is adsorbed to the respective substance adsorption membranes 13 in different modes. That is, an adsorption amount of the odor substance is different between the respective substance adsorption membranes 13. For this reason, a detection result of the detector 15 is different between the respective sensor elements 11. Therefore, pieces of measurement data by the detector 15 corresponding to the number of sensor elements 11 (substance adsorption membranes 13) included in the odor sensor 10 are generated for the certain odor substance or the composition thereof.

A measurement result output by the odor sensor 10 by measuring the certain odor substance or the composition thereof is usually specific (unique) to a specific odor substance or a composition of the odor substance. For this reason, by measuring the odor using the odor sensor 10, it is possible to identify the odor as an odor substance alone or as a composition (mixture) of odor substances.

<Odor Measurement Apparatus 50>

Figure 10:
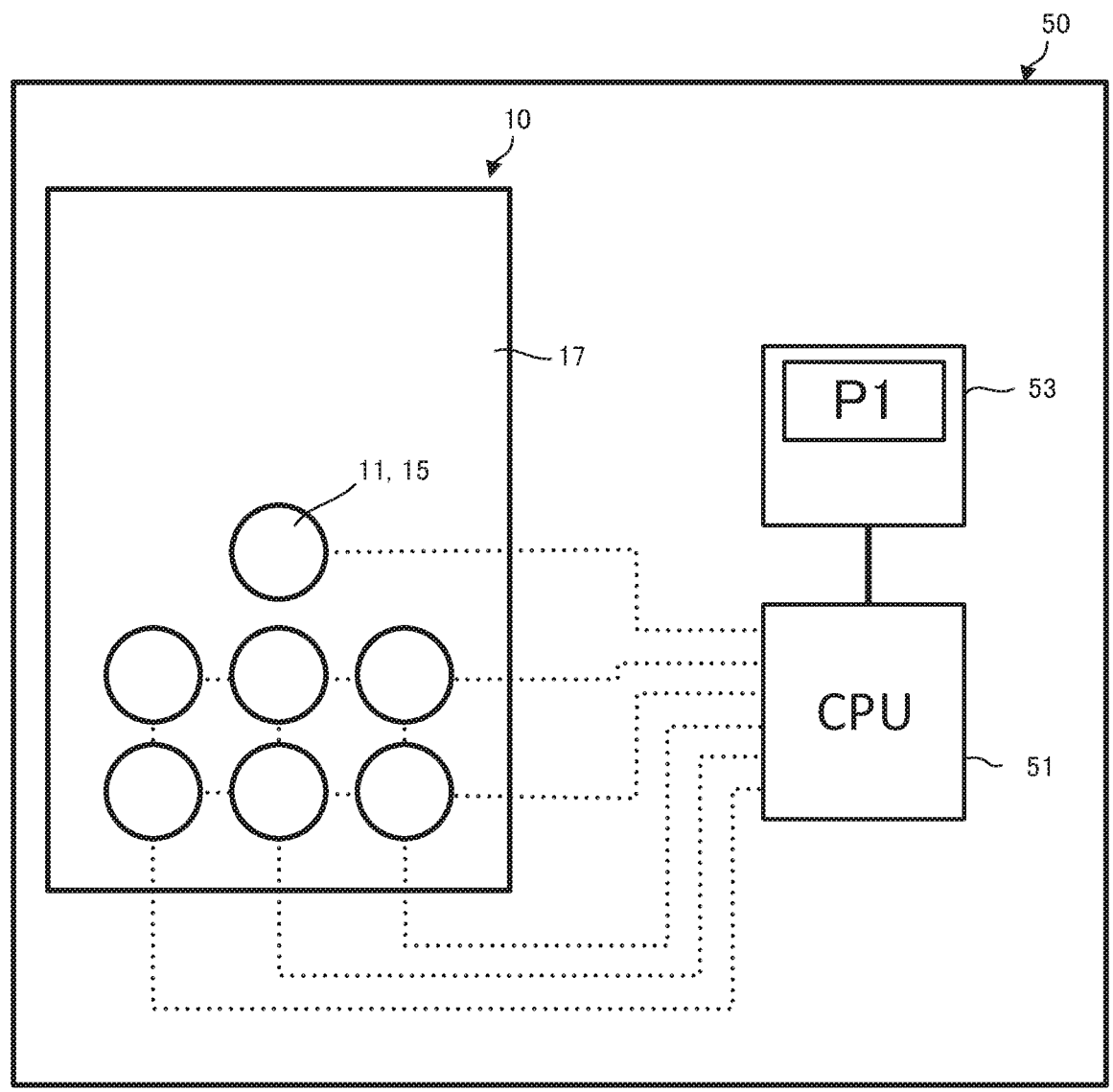
FIG. 10 is an explanatory diagram of an internal configuration of an odor measurement apparatus 50.

Next, a description will be given of an odor measurement apparatus 50 including the odor sensor 10. FIG. 10 is an explanatory diagram of an internal configuration of the odor measurement apparatus 50. The odor measurement apparatus 50 includes the odor sensor 10, an arithmetic processing device 51 connected to the odor sensor 10, and a storage device 53 connected to the arithmetic processing device 51. The measurement result measured by the odor sensor 10 can be processed in the arithmetic processing device 51, and can be stored in the storage device 53 as the odor data 5 in the form of odor data-containing data together with the main data 3. In odor measurement, by causing the arithmetic processing device 51 to execute a program P1 stored in the storage device 53, the odor measurement apparatus can function as odor measuring means. Incidentally, the acquisition of the odor data may be executed by other configurations without depending on the execution by the arithmetic processing device 51. In the first embodiment, the arithmetic processing device 51 is, for example, a central processing unit (CPU), a microprocessor (MPU), etc., and the storage device 53 is, for example, a hard disk drive (HDD), a solid-state drive (SDD), a memory (RAM), etc.

When the odor measurement apparatus 50 is used to measure the odor, it is preferable to measure the odor in the absence of the odor to be measured in order to obtain a background. By acquiring the background and subtracting the background from a measurement result of the odor, an influence of the odor to be measured can be more appropriately detected.

When the background is acquired, a state in which the odor to be measured is not present means, for example, a state in which the odor sensor 10 may not detect the odor to be measured, or the amount of detection by the odor sensor 10 is small enough to be ignored. Specifically, the state may be a state in which a generation source of the odor to be measured does not exist in a space where the odor sensor 10 is installed or is physically isolated.

Figure 11:
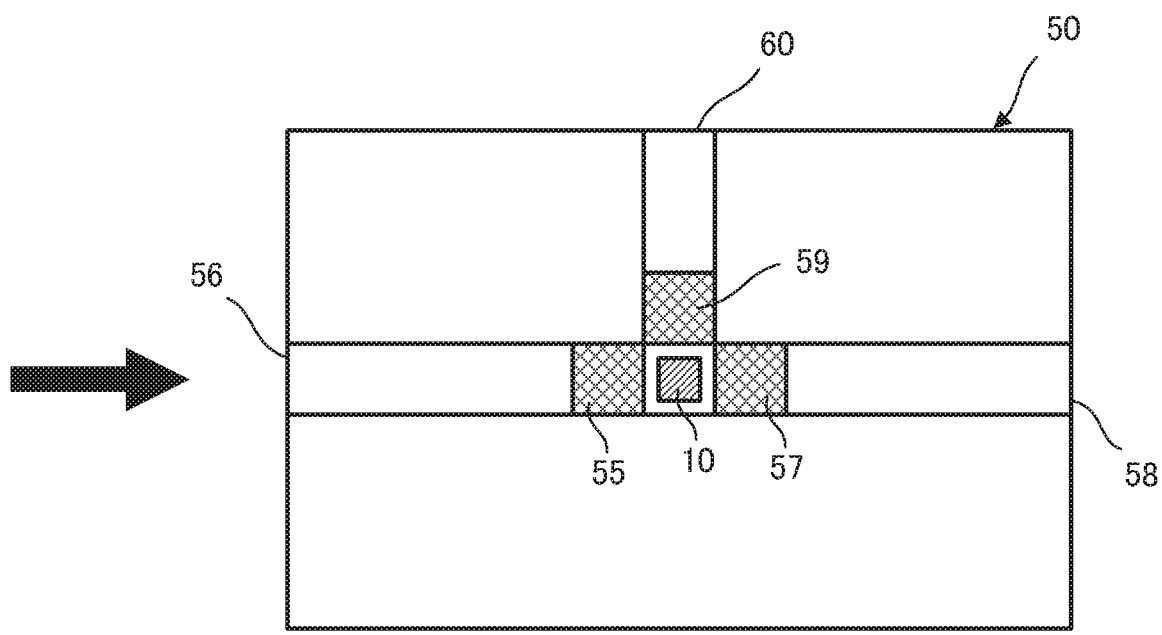
FIG. 11 is a schematic view describing air introduction of the odor measurement apparatus 50.

Examples of a configuration for physically isolating the odor sensor 10 and the odor to be measured may include the control device 55 illustrated in FIG. 11 and the like. FIG. 11 is a schematic view describing air introduction of the odor measurement apparatus 50. In FIG. 11, it is presumed that the odor to be measured is diffused from a direction of an arrow. In this instance, the air containing the odor to be measured is introduced into the odor measurement apparatus 50 from the introduction port 56 opened toward the generation source of the odor to be measured, and reaches the odor sensor 10. The control device 55 is provided between the introduction port 56 and the odor sensor 10. The control device 55 is a device that controls an inflow and outflow of the air. Examples of the control device 55 may include a sealing valve configured to be openable and closable, a fan, etc. In FIG. 11, an external shape of the odor measurement apparatus 50 is simplified and illustrated as a rectangle for convenience of description. However, the external shape of the odor measurement apparatus 50 is not limited thereto.

As illustrated in FIG. 11, the odor measurement apparatus 50 preferably has a ventilation opening 58 which is open in a different direction from that of the introduction port 56, that is, a different direction from a direction in which the odor to be measured is introduced. When the air is introduced from the different direction from the introduction direction of the odor to be measured, the air not containing the odor to be measured or containing the odor to be measured but at a detection amount of which is small enough to be negligible, can be introduced to the odor sensor 10. In this way, it is possible to acquire a more appropriate background value. A control device 57 may be disposed between the ventilation opening 58 and the odor sensor 10.

An opening other than the introduction port such as the ventilation opening 58 is not limited to an opening on an extension of a straight line connecting the introduction port 56 and the odor sensor 10 such as the ventilation opening 58, and it is sufficient that the opening is in a different direction from the introduction direction of the odor to be measured. For example, the opening may be a ventilation opening 60. The ventilation opening 58 and the ventilation opening 60 may coexist. A control device 59 is disposed between the ventilation opening 60 and the odor sensor 10.

The control devices 55, 57, and 59 are not particularly limited as long as the control devices can control the inflow and outflow of air. Examples thereof may include a seal valve configured to be openable and closable, a shutter, a fan that can rotate in a forward direction and a reverse direction, etc. When the control devices 55, 57, and 59 coexist, the respective control devices may have the same configuration or have different configurations. In addition, the control devices 55, 57, and 59 may operate in conjunction with each other. For example, when all the control devices 55, 57, and 59 are seal valves, and the control device 55 is in an open state, it is preferable that the control device 57 is in an open state, and the control device 59 is in a closed state. In this way, the air introduced from the introduction port 56 passes through the odor sensor 10, and then is discharged from the ventilation opening 58. On the other hand, when the control device 55 is in a closed state, it is preferable that the control device 57 is in a closed state, and the control device 59 is in an open state. In this way, when a measurement value of a background is acquired, air not containing the odor to be measured can be introduced from the ventilation opening 60 and measured by the odor sensor 10.

As a configuration in which the odor sensor 10 and the generation source of the odor to be measured are physically isolated from each other, it is possible to adopt a configuration in which a position of the odor sensor 10 is variable. For example, only when the odor sensor 10 is arranged at a distal end of an arm, and the odor to be measured is measured, it is possible to move the odor sensor 10 to the vicinity of the generation source of the odor to be measured. At the time of acquiring the background, it is possible to use a measurement result of the odor at a place sufficiently away from the generation source of the odor to be measured.

<Composite Data Generation Device>

A composite data generation device includes main data generating means that generates the main data 3 and the odor sensor 10. The composite data generation device is a device capable of generating the odor data-containing data 1 as composite data based on the data structure.

Hereinafter, the composite data generation device will be described in detail using Examples.

EXAMPLE 1

As Example 1, a description is given of a case in which the composite data generation device is a diagnostic apparatus 100, and the main data is image data. As Example 1, a description is given of a case in which the image data is specifically data of a computed tomography image (CT image) with reference to drawings. The image is not limited to the CT image, and it is possible to adopt an X-ray image from an X-ray imaging device and various other images by image diagnosis using radiation.

Figure 12:
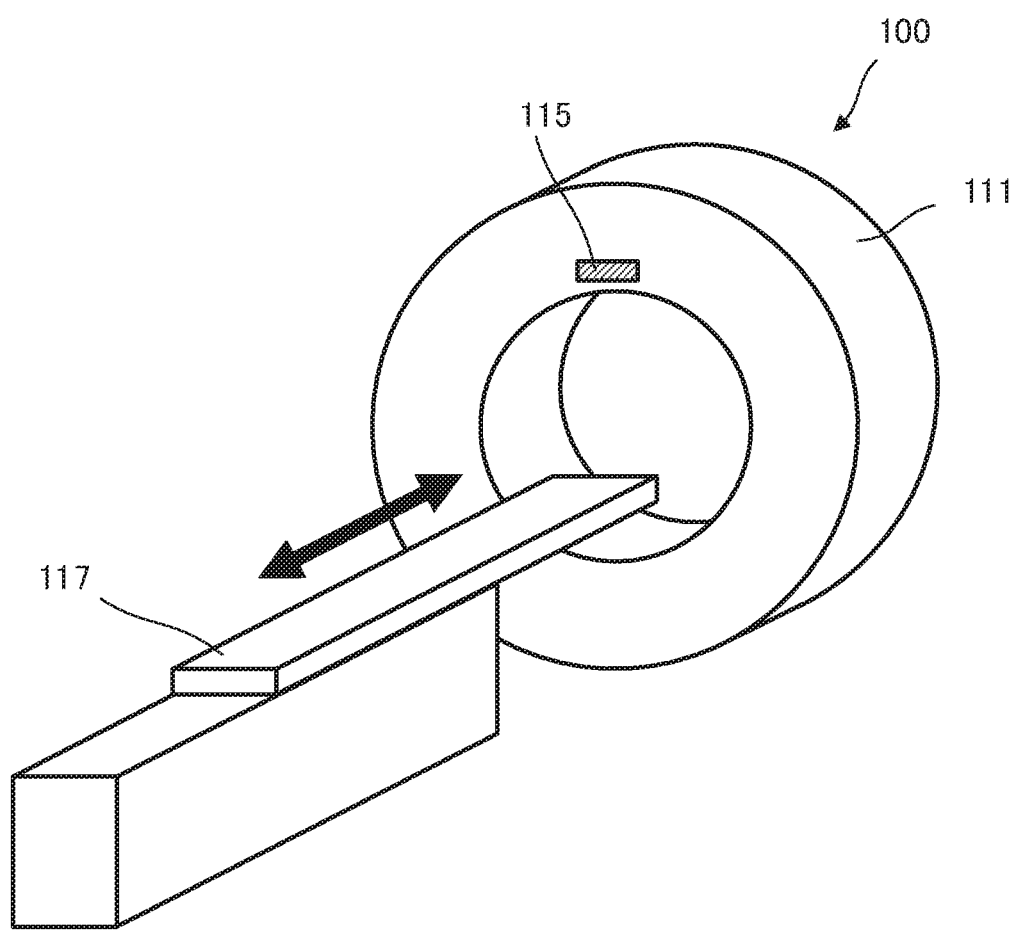
FIG. 12 is a schematic view illustrating a diagnostic apparatus 100 of Example 1.

FIG. 12 is a schematic view illustrating the diagnostic apparatus 100 of Example 1. Specifically, the diagnostic apparatus 100 of FIG. 12 is a computed tomography apparatus (CT apparatus). The diagnostic apparatus 100 includes a cylindrical gantry 111, and a bed 117 which conveys at least a part of a body of a subject to a cylindrical hollow portion of the gantry 111 and allows insertion into the hollow portion. The bed 117 is configured to be movable in parallel in a direction of insertion into the hollow portion of the gantry 111. This parallel movement can be performed such that insertion into the hollow portion of the gantry 111 is allowed while the subject is lying on the bed 117. The gantry 111 internally includes an X-ray irradiation device 112 and an X-ray detection device 113. An X-ray emitted from the X-ray irradiation device 112 is irradiated to the subject moved to the hollow portion of the gantry 111, and an X-ray transmitted through the subject is detected by the X-ray detection device 113. In this way, a diagnostic image of the subject can be obtained. The diagnostic image can be output as the image data 103.

The diagnostic apparatus 100 includes an odor measurement apparatus 115 in a part of the gantry 111. The odor measurement apparatus 115 can detect mouth odor and body odor emitted by the subject. For example, the odor measurement apparatus 115 can be disposed to be exposed in the vicinity of the hollow portion of the gantry 111 and on a surface of a housing of the gantry 111. In this case, it is possible to detect an odor of an examination room when the subject is not therein as an odor of the background.

The odor measurement apparatus 115 may include the introduction port 56, the ventilation openings 58 and 60, the control devices 55, 57, and 59, etc. described above. When the odor measurement apparatus 115 is disposed inside the gantry 111, the introduction port 56 opens toward the hollow portion of the gantry 111, that is, a portion into which the subject is inserted. In this case, the ventilation openings 58 and 60 open in a different direction from that of the hollow portion of the gantry 111, that is, toward the outside of the gantry 111.

The odor measurement apparatus 115 may be disposed at any position without being limited to the gantry 111 as long as it is possible to detect the mouth odor and body odor emitted by the subject. For example, the odor measurement apparatus 115 may be disposed on the bed 117, or may be disposed on a separate arm independent of the gantry 111 and the bed 117.

The odor measurement apparatus 115 has a plurality of sensor elements 155*a*, 155*b*, and 155*c*. Even though only three sensor elements 155*a*, 155*b* and 155*c* are illustrated in FIG. 13 for convenience of description, the number of sensor elements is not limited to three.

Figure 13:
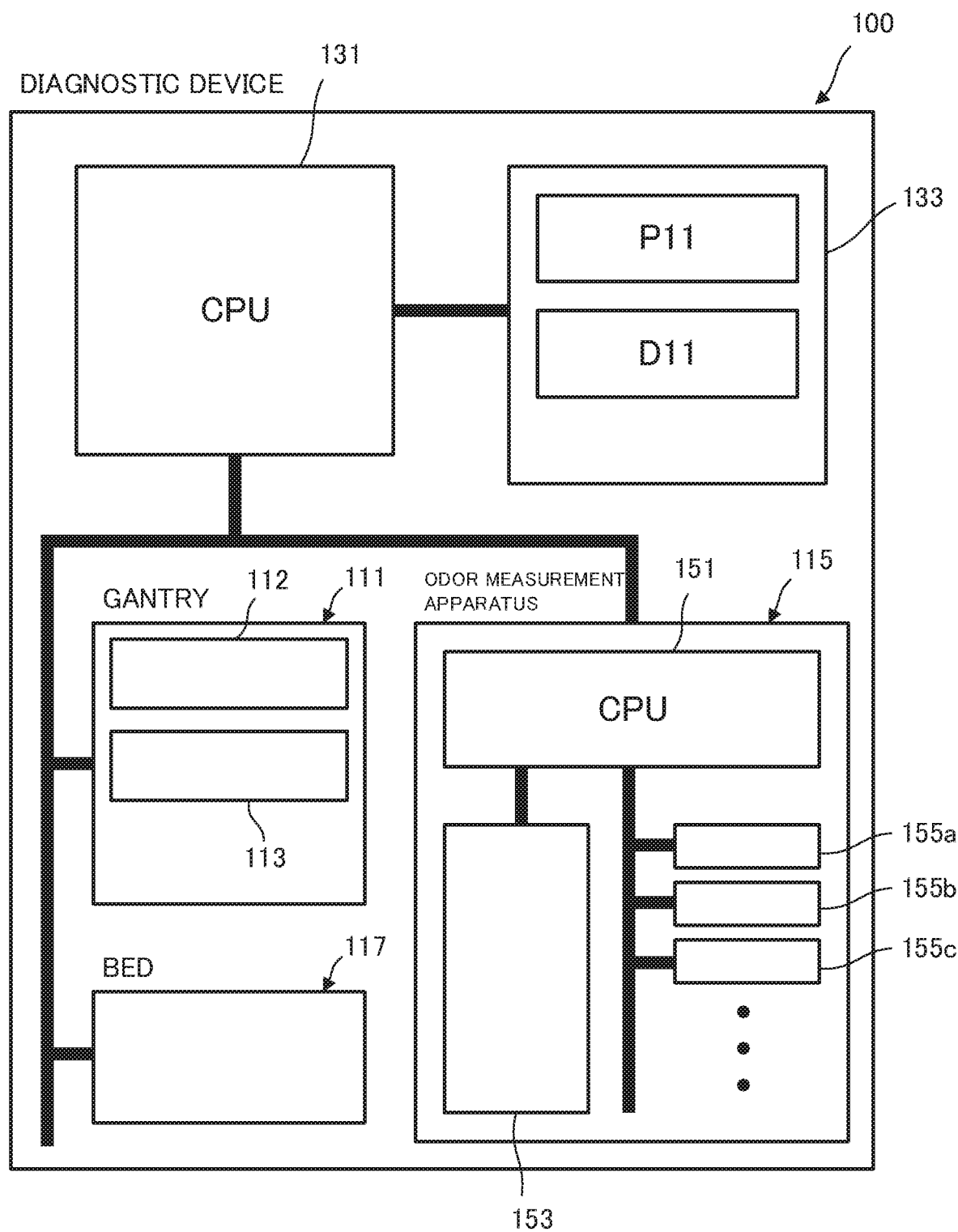
FIG. 13 is a block diagram schematically illustrating a first example of an internal configuration of the diagnostic apparatus 100 of Example 1.

FIG. 13 is a block diagram schematically illustrating a first example of an internal configuration of the diagnostic apparatus 100 of Example 1. As illustrated in FIG. 13, in the diagnostic apparatus 100, an arithmetic processing device (CPU) 131, a storage device 133, the gantry 111, the bed 117, and the odor measurement apparatus 115 are communicably connected to one another. The CPU 131 can control behaviors of the storage device 133, the gantry 111, the bed 117, and the odor measurement apparatus 115. The storage device 133 stores a program P11 and a database D11. By executing the program P1, the CPU 131 can exhibit a function of acquiring a diagnostic image, a function of measuring the odor emitted by the subject, etc.

The CPU 131 can control parallel movement of the bed 117 on which the subject rides, and can move the bed 117 so that a diagnostic site is inserted into an X-ray irradiation area located in the hollow portion of the gantry 111. Subsequently, the CPU 131 controls an X-ray diagnostic apparatus of the gantry 111 to irradiate an X-ray toward the diagnostic site of the subject. The transmitted X-ray is detected by the detector of the gantry 111. The image data 103 of the diagnostic image is stored by the CPU 131 in a predetermined area of the database D11 in the storage device 133. In this way, the diagnostic apparatus 100 can acquire the diagnostic image.

The CPU 131 can control the odor measurement apparatus 115 by executing the program P11 to acquire and measure the mouth odor, the body odor, or both the mouth odor and the body odor of the subject using the odor measurement apparatus 115 simultaneously with acquisition of the diagnostic image described above or before/after acquisition of the diagnostic image. As the odor measurement apparatus 115, the above-mentioned odor sensor 10 can be used. The CPU 131 can generate the odor data 105 based on the measurement result measured by the odor measurement apparatus 115 by executing the program P11.

Figure 14:
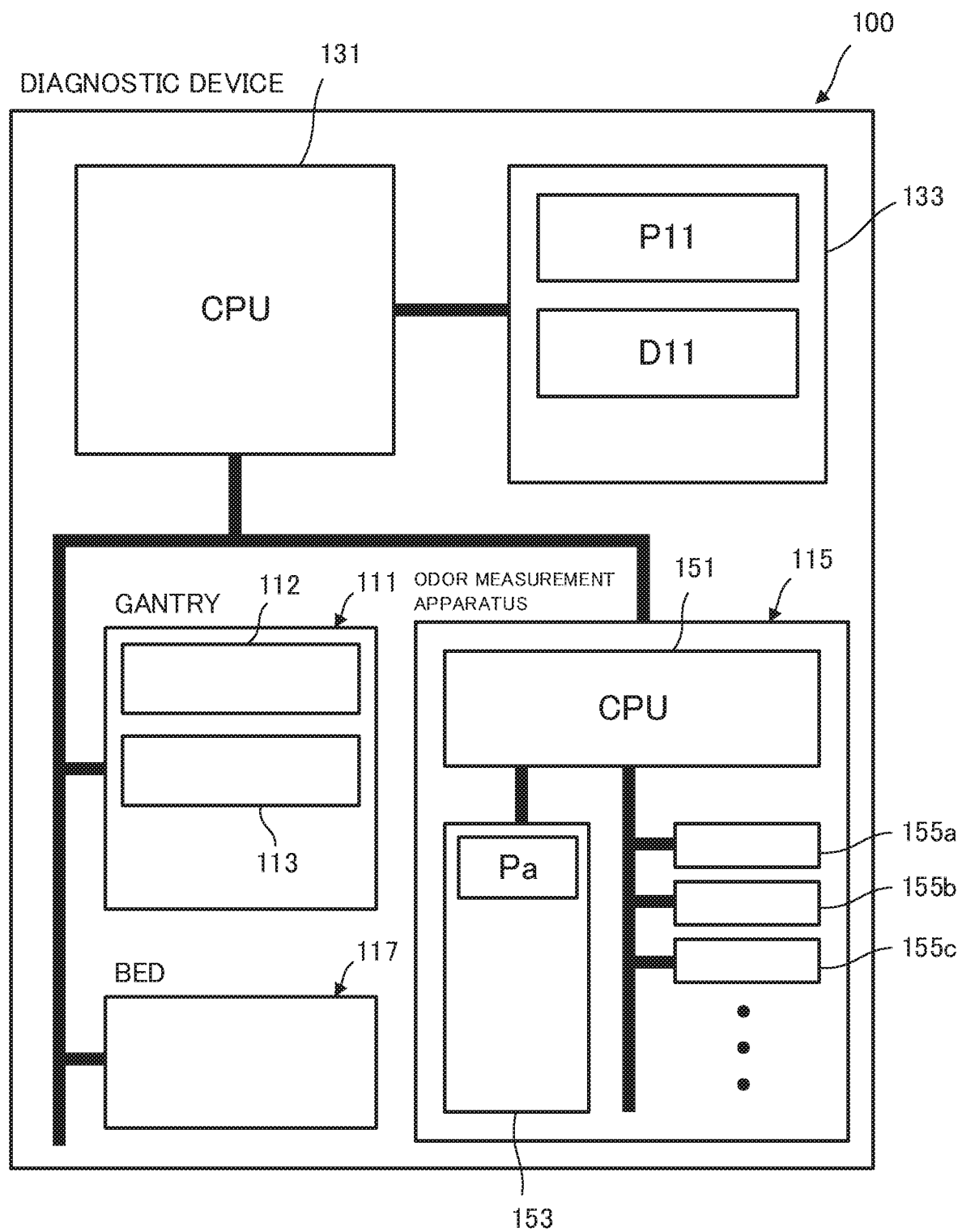
FIG. 14 is a block diagram schematically illustrating a second example of the internal configuration of the diagnostic apparatus 100 of Example 1.

FIG. 14 is a block diagram schematically illustrating a second example of the internal configuration of the diagnostic apparatus 100 of Example 1. As illustrated in FIG. 14, generation of the odor data 105 by the CPU 131 executing the program P1 can be realized by the CPU 151 provided in the odor measurement apparatus 115 executing a program Pa stored in the storage device 153 without using the CPU 131. In this way, a processing process of the measurement result by each of the sensor element 155a, 155b, and 155c of the odor sensor 116, etc. can be completed in the odor measurement apparatus 115.

The odor measurement apparatus 115 includes the arithmetic processing device (CPU) 151 and the storage device 153 in addition to the sensor element 155a, 155b, and 155c, etc. The CPU 151 can acquire a measurement result obtained by each of the sensor element 155a, 155b, and 155c, etc. and store the acquired measurement result in the storage device 153. The CPU 151 may pass the measurement result to the CPU 131 of the diagnostic apparatus 100 and store the measurement result in the storage device 133 without storing the measurement result in the storage device 153.

The storage device 133 stores a database D11 in which various types of information related to CT examination such as a subject name, a date and time of diagnosis, a diagnostic image, odor data, a definite diagnostic, a symptom/case, an etiology, etc. are associated with each other and stored. The odor data 105 stored in the database D11 may be the odor measurement result (raw data) acquired by the odor sensor 116, or may be odor data processed based on the odor measurement result. As described above, by associating the odor data 105 with the various types of information related to the CT examination, it is possible to analyze a relationship between the odor and the diagnosis and symptom. For example, when odor data with regard to a subject undergoing a specific diagnosis has a feature, a subject whose odor data having the feature is measured from a body odor or mouth odor may receive the specific diagnosis.

FIG. 15 is the database D11 of Example 1. The odor data 5 and data of a subject name, a date and time of diagnosis, definite diagnosis, a symptom/case, and an etiology are stored in the database D11 in association with data of the diagnostic image obtained by CT examination. Referring to the odor data 5, a plurality of pieces of odor data 5 may be stored in the database D11 before/after treatment or according to a site in which the odor is measured.

The database D11 may be stored not only in the storage device 133, but also in a cloud server to which the diagnostic apparatus 100 is connected via the Internet. When the database D11 is stored in the cloud server, the diagnostic apparatus 100 may directly store each piece of information stored in the database D11 in the database D11 on the cloud server without storing the information in the storage device 133.

Figure 16:
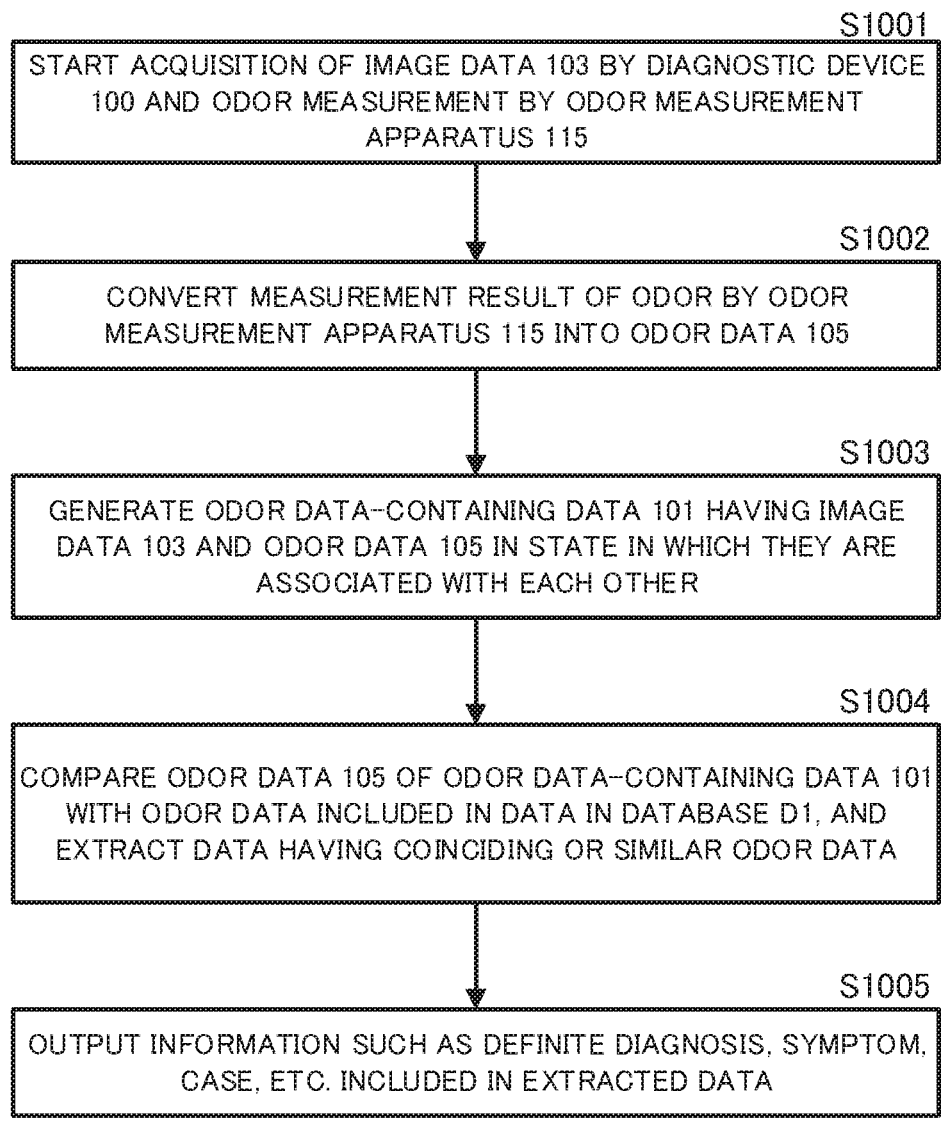
FIG. 16 is a flowchart illustrating processes by the diagnostic apparatus 100 of Example 1.

Here, a description will be given of a flow of processing of CT examination and acquisition of the odor data 105 in the diagnostic apparatus 100 with reference to FIG. 16. FIG. 16 is a flowchart illustrating processes by the diagnostic apparatus 100 of Example 1. In step (hereinafter, "S") 1001, the diagnostic apparatus 100 starts acquisition of the image data 103, and the odor measurement apparatus 115 starts odor measurement. Specifically, the CPU 131 controls the X-ray irradiation device 112, the X-ray detection device 113, the bed 117, and the odor measurement apparatus 115. When the CT examination is started, the CPU 131 operates the odor measurement apparatus 115 to measure the odor by the odor sensor 116. Subsequently, the CPU 131 operates the bed 117, the X-ray irradiation device 112, and the X-ray detection device 113 to acquire a CT image as the image data 103. It is to be noted that one of odor measurement by the odor measurement apparatus 115 and acquisition of the image data 103 may be started without waiting for the other one to be completed, and operation time zones thereof may overlap. In addition, acquisition of the image data 103 may be started prior to odor measurement.

In S1002, the CPU 131 processes the measurement result of the odor by the odor measurement apparatus 115 and converts the processed measurement result into the odor data 105. Specifically, the CPU 131 acquires the measurement result of the odor by the odor measurement apparatus 115, calculates a difference thereof, and obtains the odor data 105 as processed data.

In S1003, the CPU 131 generates odor data-containing data 101 having the image data 103 and the odor data 105 in a state in which the image data 103 and the odor data 105 are associated with each other.

In S1004, the CPU 131 compares the odor data 105 of the odor data-containing data 101 with the odor data included in the data in the database D11. Then, in the compared data, data having coinciding or similar odor data is extracted from the database D11. The database D11 may be stored in the storage device 133 or may be stored in a cloud server communicably connected via the Internet. When the database D11 is stored in the cloud server, the CPU 131 can download the extracted data and store the data in the storage device 133.

In S1005, the CPU 131 can output information such as a definite diagnosis, a symptom, a case, etc. included in the extracted data to, for example, a display screen (not illustrated) of the diagnostic apparatus 100. In this way, in addition to performing CT examination of the subject, it is possible to refer to a diagnostic name, a symptom, a case, etc. in the case of another subject whose odor data having a similar feature to that of the odor data of the subject is measured.

EXAMPLE 2

As Example 2, a description is given of a case in which the composite data generation device is a portable information terminal 200 and the main data 3 is location data. The portable information terminal 200 is a portable information terminal 200 including a global positioning system (GPS) device 213, and more specifically, can be a smartphone, a tablet terminal, or a portable terminal such as a mobile phone including a GPS device 213. The portable information terminal 200 includes an odor measurement apparatus 215 in addition to the GPS device 213. The portable information terminal 200 may further include a display screen 211, an imaging device 217, and an atmospheric pressure measurement apparatus 219.

Figure 17:
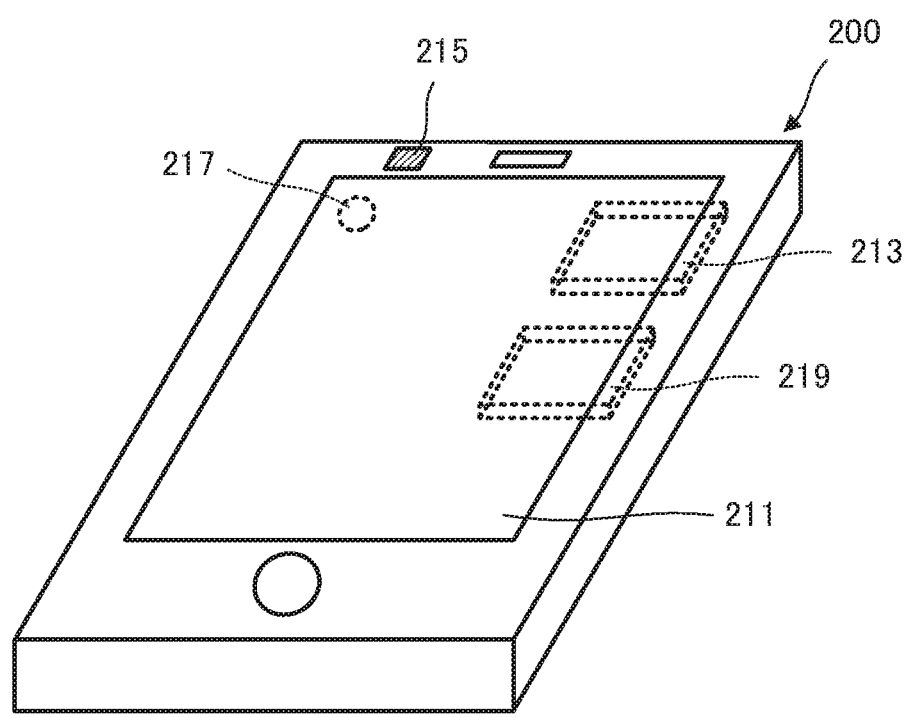
FIG. 17 is a schematic view illustrating a portable information terminal 200 of Example 2.

FIG. 17 is a schematic view illustrating the portable information terminal 200 of Example 2. As illustrated in FIG. 17, since the portable information terminal 200 includes the odor measurement apparatus 215, an odor of an atmospheric air in which the portable information terminal 200 is located can be measured. The odor measurement apparatus 215 may have the introduction port 56, the ventilation openings 58 and 60, the control devices 55, 57, and 59, etc. mentioned above. When the odor measurement apparatus 215 is disposed inside a housing of the portable information terminal 200, the introduction port 56 is open in any surface of the housing of the portable information terminal 200. In this case, the ventilation openings 58 and 60 are open in a surface different from the surface in which the introduction port 56 of the housing of the portable information terminal 200 is open.

The introduction port 56 of the odor measurement apparatus may be disposed on the same surface as that of the imaging device 217. The imaging device 217 is, for example, a camera. When the introduction port 56 of the odor measurement apparatus 215 is disposed on the same surface as that of the imaging device 217, a possibility that the generation source of the odor to be measured will be reflected in an image captured by the imaging device 217 increases.

The odor measurement apparatus 215 has a plurality of sensor elements 255a, 255b, and 255c. Even though only three sensor elements 255a, 255b and 255c are illustrated in FIG. 18 for convenience of description, the number of sensor elements is not limited to three.

Figure 18:
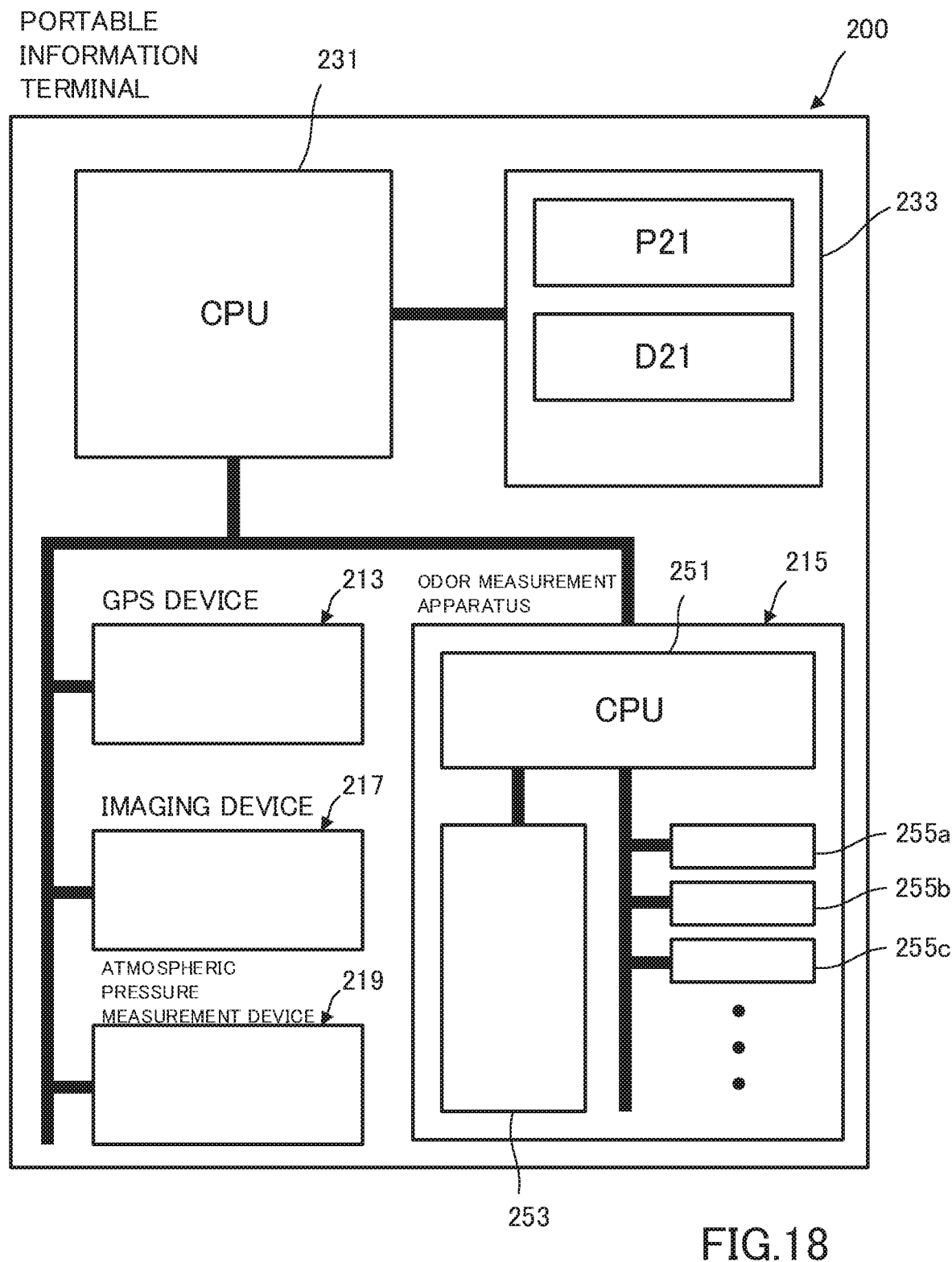
FIG. 18 is a block diagram schematically illustrating an internal configuration of the portable information terminal 200 of Example 2.

FIG. 18 is a block diagram schematically illustrating an internal configuration of the portable information terminal 200 of Example 2. As illustrated in FIG. 18, in the portable information terminal 200, the arithmetic processing device (CPU) 231, the storage device 233, the GPS device 213, the imaging device 217, the atmospheric pressure measurement apparatus 219, and the odor measurement apparatus 215 are communicably connected to each other. The CPU 231 can control behaviors of the storage device 233, the GPS device 213, the imaging device 217, the atmospheric pressure measurement apparatus 219, and the odor measurement apparatus 215. The storage device 233 stores a program P21 and a database D21. When the CPU 231 executes the program P21, the portable information terminal 200 can exhibit a function of acquiring the location data 203, a function of capturing an image, a function of measuring an atmospheric pressure, a function of measuring the odor in the atmospheric air, etc.

The CPU 231 can control the odor measurement apparatus 215 by executing the program P21 to acquire an atmospheric air and measure an odor therein using the odor measurement apparatus 215 simultaneously with acquisition of the location data 203 or before/after acquisition of the location data 203. As the odor measurement apparatus 215, the above-mentioned odor sensor 10 can be used. The CPU 231 can generate odor data 205 based on a measurement result measured by the odor measurement apparatus 215 by executing the program P21.

The odor measurement apparatus 215 includes the arithmetic processing device (CPU) 251 and the storage device 253 in addition to the sensor element 255a, 255b, and 255c, etc. The CPU 251 can acquire a measurement result obtained by each of the sensor element 255a, 255b, and 255c, etc. and store the acquired measurement result in the storage device 253. The CPU 251 may pass the measurement result to the CPU 231 of the portable information terminal 200 and store the measurement result in the storage device 233 without storing the measurement result in the storage device 253.

The storage device 233 stores the database D21 in which various types of information such as the location data 203 of latitude and longitude, atmospheric pressure information, odor data, a measurement time, image data, etc. are associated with each other and stored. The odor data 205 stored in the database D21 may be the odor measurement result (raw data) acquired by the odor measurement apparatus 215, or may be the odor data 5 processed based on the odor measurement result. As described above, by associating the odor data 205 with the various types of information acquired by the portable information terminal 200, it is possible to associate the odor with position information. For example, by expanding the database D21 in which the odor is associated with the position information, it is possible to comprehend a distribution of the odor measured using the portable information terminal 200 in a specific place on a map. In addition, it is possible to detect a place where an odor having the same or similar odor data as or to the odor data measured by the portable information terminal 200, etc. is generated by a search using the odor data as a key.

By associating atmospheric pressure information measured by the atmospheric pressure measurement apparatus 219 together with the odor data 205 and the location data 203, it is possible to comprehend an atmospheric pressure environment in which the odor data measured by the odor measurement apparatus 215 is measured. In addition, by associating image data captured by the imaging device 217 together with the odor data 205 and the location data 203, it is possible to refer to an image of the environment to verify the environment where the measured odor data is generated. For example, by associating image data, it may be possible to acquire an image of the generation source the odor.

Figure 19:
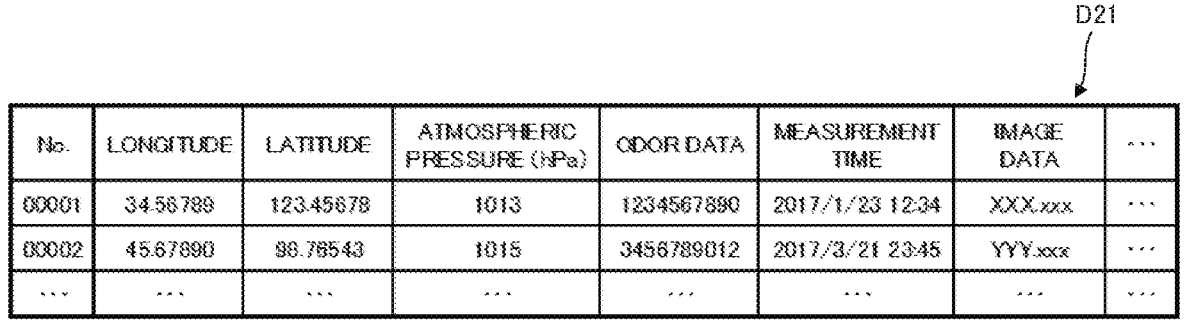
FIG. 19 is a database D21 of Example 2.

FIG. 19 is a database D21 of Example 2. In the database D21, the odor data 205, longitude, latitude, the atmospheric pressure, a measurement time, and image data are stored in association with the location data 203 acquired by the GPS device 213. The database D21 may be stored not only in the storage device 233 but also in a cloud server to which the portable information terminal 200 is connected via the Internet. When the database D21 is stored in the cloud server, the portable information terminal 200 may directly store each piece of information stored in the database D21 in the database D21 on the cloud server without storing the information in the storage device 233.

Figure 20:
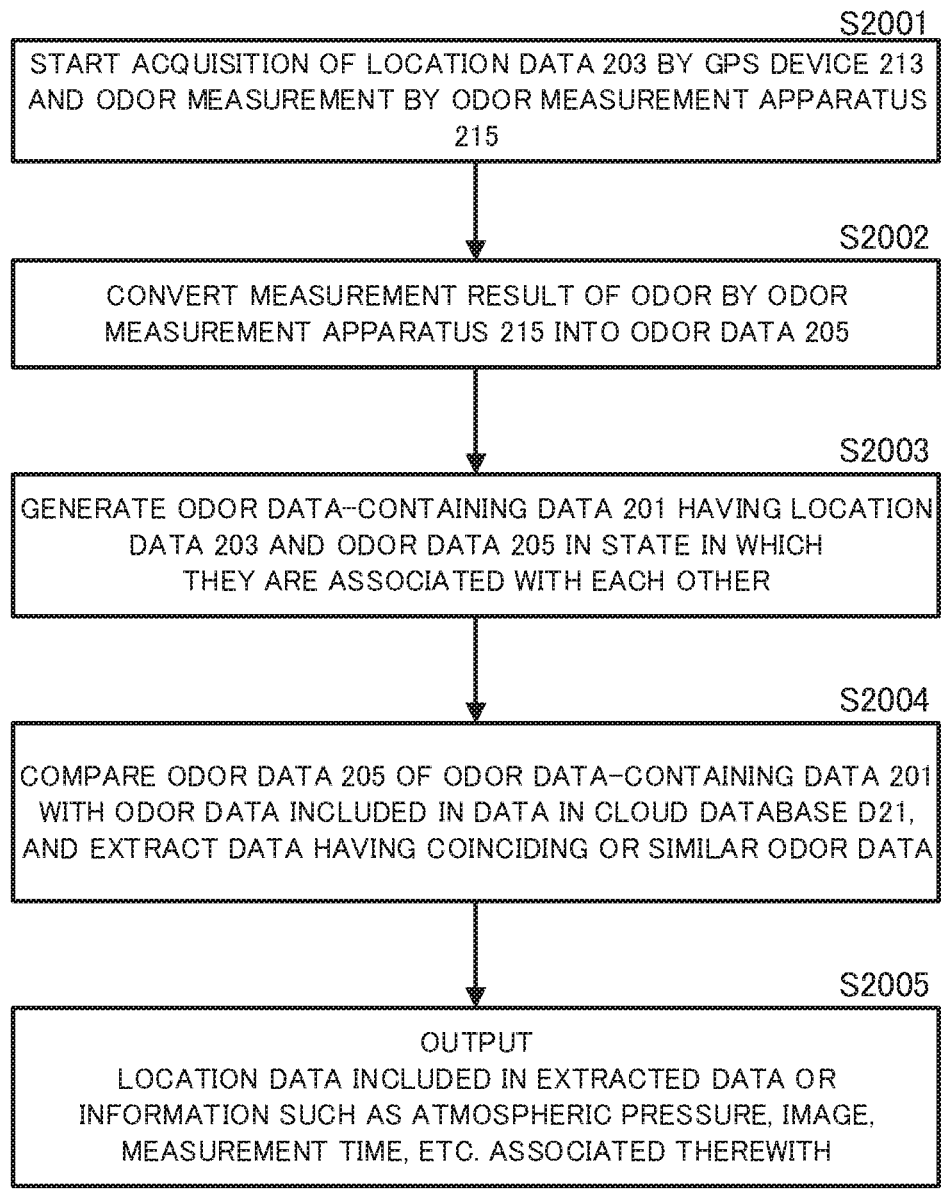
FIG. 20 is a flowchart illustrating processes by the portable information terminal 200 of Example 2.

Here, a description will be given of a flow of processing of acquisition of the location data 203, etc. and acquisition of the odor data 205 in the portable information terminal 200 with reference to FIG. 20. FIG. 20 is a flowchart illustrating processes by the portable information terminal 200 of Example 2. In S2001, the portable information terminal 200 starts acquisition of the location data 203 by the GPS device 213, and the odor measurement apparatus 215 starts odor measurement. Specifically, the CPU 231 controls the GPS device 213 and records the location data 203. It is to be noted that one of odor measurement by the odor measurement apparatus 115 and acquisition of the location data 203 may be started without waiting for the other one to be completed, and operation time zones thereof may overlap. In addition, acquisition of the location data 203 may be started prior to odor measurement. In this instance, measurement of the atmospheric pressure by the atmospheric pressure measurement apparatus 219 and image capturing by the imaging device 217 may be performed simultaneously with or before/after acquisition of the location data 203 or odor measurement.

In S2002, the CPU 231 processes the measurement result of the odor by the odor measurement apparatus 215, and acquires the odor data 205. Specifically, the CPU 231 acquires the measurement result of the odor by the odor measurement apparatus 215, calculates a difference thereof, and obtains the odor data 205 as processed data.

In S2003, the CPU 231 generates odor data-containing data 201 having the location data 203 and the odor data 205 in a state in which the location data 203 and the odor data 205 are associated with each other.

In S2004, the CPU 231 compares the odor data 205 of the odor data-containing data 201 with the odor data included in the data in the database D21. Then, in the compared data, data having coinciding or similar odor data is extracted from the database D21. The database D21 may be stored in the storage device 233 or may be stored in a cloud server communicably connected via the Internet. When the database D21 is stored in the cloud server, the CPU 231 can download the extracted data and store the data in the storage device 233.

In S2005, the CPU 231 can output information such as a position, an atmospheric pressure, an image, a measurement time, etc. included in the extracted data to, for example, the display screen 211 of the portable information terminal 200.

EXAMPLE 3

As Example 3, a description will be given of a case in which the composite data generation device is a movie recording terminal 300 and the main data 3 is movie data. The movie recording terminal 300 is the movie recording terminal 300 including a movie recording device 313, and specifically may be a video camera, a smartphone, a tablet terminal, an action camera, etc. The movie recording terminal 300 includes an odor measurement apparatus 315 in addition to the movie recording device 313. The movie recording terminal 300 may further include a lens 311 and an audio recording device 317.

Figure 21:
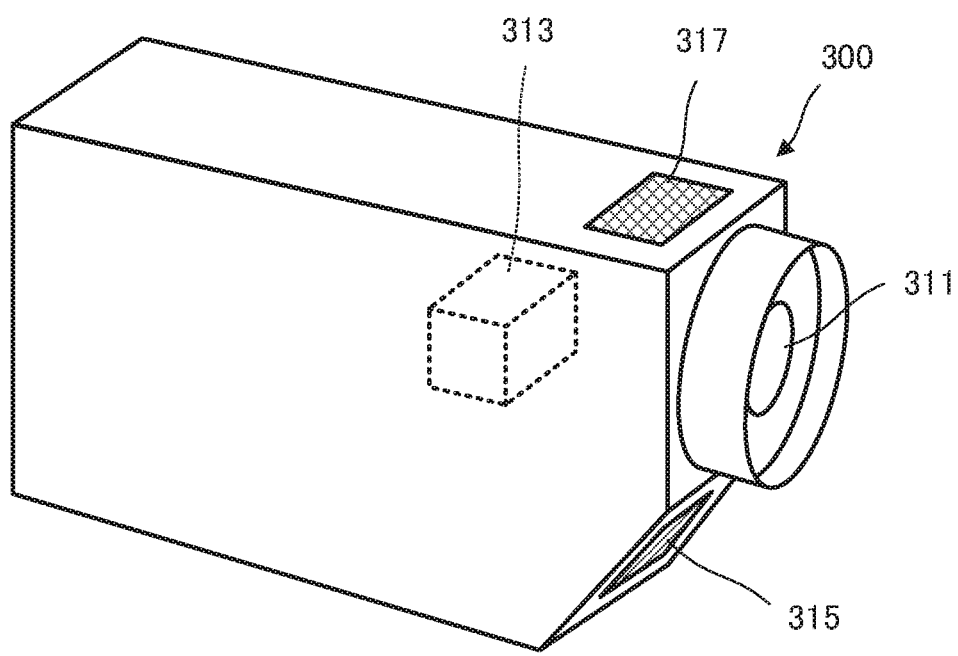
FIG. 21 is a schematic view illustrating a movie recording terminal 300 of Example 3.

FIG. 21 is a schematic view illustrating the movie recording terminal 300 of Example 3. As illustrated in FIG. 21, the movie recording terminal 300 includes the odor measurement apparatus 315, and thus it is possible to measure an odor in an atmospheric air in which the movie recording terminal 300 is located. The odor measurement apparatus 315 may have the introduction port 56, the ventilation openings 58 and 60, the control devices 55, 57, and 59, etc. mentioned above. When the odor measurement apparatus 315 is disposed inside a housing of the movie recording terminal 300, the introduction port 56 is open in any surface of the housing of the movie recording terminal 300. In this case, the ventilation openings 58 and 60 are open in a surface different from the surface in which the introduction port 56 of the housing of the movie recording terminal 300 is open.

The introduction port 56 of the odor measurement apparatus 315 is preferably disposed on the same surface as that of the lens 311 or a surface directed in an approximate direction. When the introduction port 56 of the odor measurement apparatus 315 is disposed in the same direction as that of the lens 311 or directed in an approximate direction, a possibility that the generation source of the odor to be measured will be reflected in an image captured by the movie recording device 313 through the lens 311 increases.

The odor measurement apparatus 315 has a plurality of sensor elements 355a, 355b, and 355c. Even though only three sensor elements 355a, 355b, and 355c are illustrated in FIG. 22 for convenience of description, the number of sensor elements is not limited to three.

Figure 22:
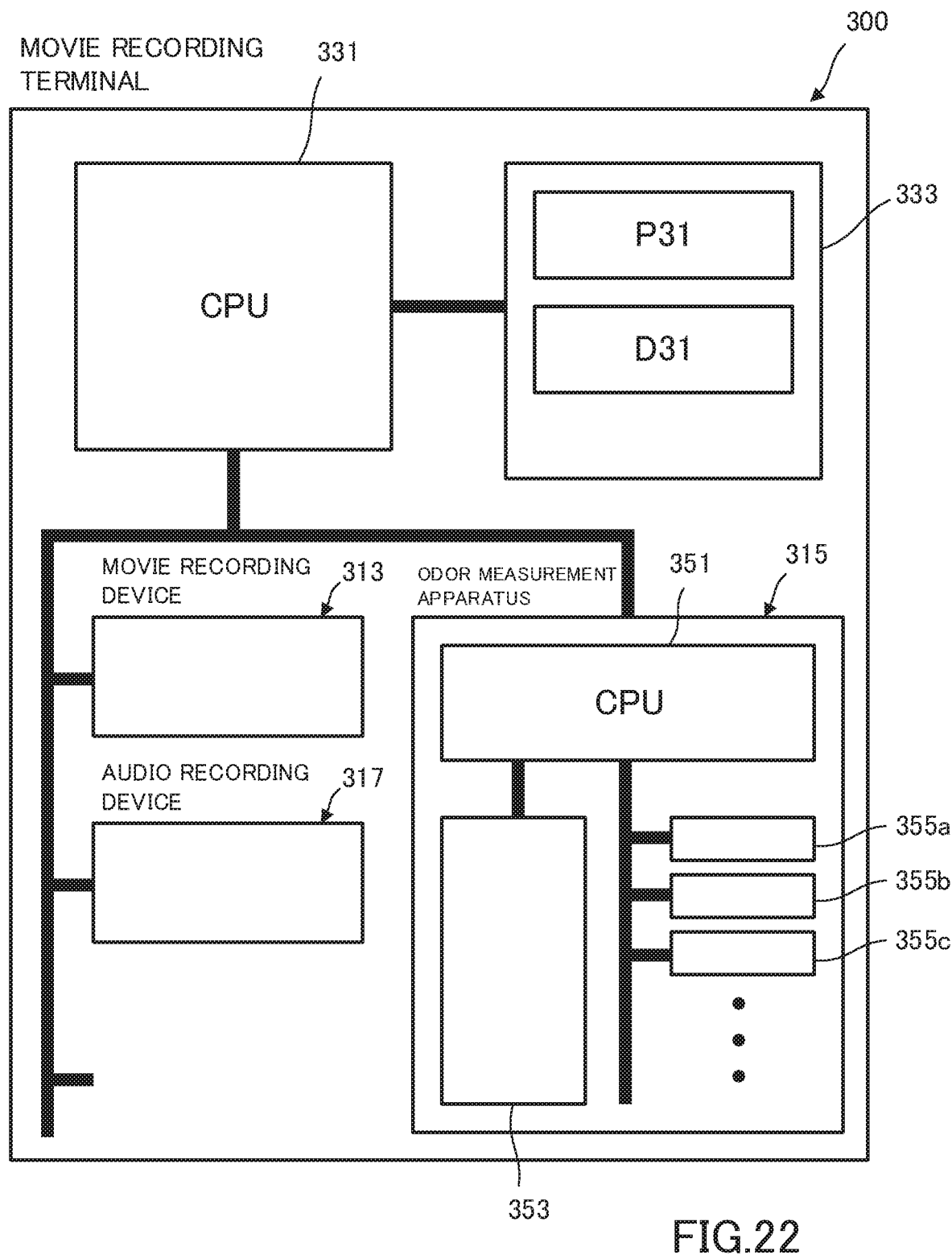
FIG. 22 is a block diagram schematically illustrating an internal configuration of the movie recording terminal 300 of Example 3.

FIG. 22 is a block diagram schematically illustrating an internal configuration of the movie recording terminal 300 of Example 3. As illustrated in FIG. 22, in the movie recording terminal 300, an arithmetic processing device (CPU) 331, a storage device 333, a movie recording device 313, an audio recording device 317, and an odor measurement apparatus 315 are communicably connected to each other. The CPU 331 can control behaviors of the storage device 333, the movie recording device 313, the audio recording device 317, and the odor measurement apparatus 315. The storage device 333 stores a program P31 and a database D31. When the CPU 331 executes the program P31, the movie recording terminal 300 can exhibit a function of acquiring movie data 303, a function of recording audio data 307, a function of measuring odor data 305 in the atmospheric air, etc.

The CPU 331 can control the odor measurement apparatus 315 by executing the program P31, and acquire an atmospheric air and measure an odor therein using the odor measurement apparatus 315 simultaneously with capturing of the movie, in the middle of capturing of the movie, or before/after capturing of the movie. As the odor measurement apparatus 315, it is possible to use the odor sensor 10 mentioned above. The CPU 331 can generate the odor data 305 based on a measurement result measured by the odor measurement apparatus 315 by executing the program P31.

The odor measurement apparatus 315 includes the arithmetic processing device (CPU) 351 and the storage device 353 in addition to the sensor elements 355a, 355b, and 355c, etc. The CPU 351 can acquire a measurement result obtained by each of the sensor element 355a, 355b, and 355c, etc. and store the acquired measurement result in the storage device 353. The CPU 351 may pass the measurement result to the CPU 331 of the movie recording terminal 300 and store the measurement result in the storage device 333 without storing the measurement result in the storage device 353.

The storage device 333 stores the database D31 in which various types of information such as the movie data 303, the odor data 305, the audio data 307, etc. are associated with each other and stored. The odor data 305 stored in the database D31 may be the odor measurement result (raw data) acquired by the odor measurement apparatus 315, or may be the odor data 5 processed based on the odor measurement result. As described above, by associating the odor data 305 with the various types of information acquired by the movie recording terminal 300, it is possible to associate the odor with the movie data 303. For example, by expanding the database D31 in which the odor is associated with the position information, it is possible to comprehend a situation in which the odor measured using the movie recording terminal 300 in a specific place is generated. In addition, it is possible to detect a situation in which an odor having the same or similar odor data as or to the odor data 305 measured by the movie recording terminal 300, etc. is generated by a search using the odor data as a key. It is possible to associate the audio data 307 recorded using the audio recording device 317 together with the odor data 305 and the movie data 303.

Figure 23:
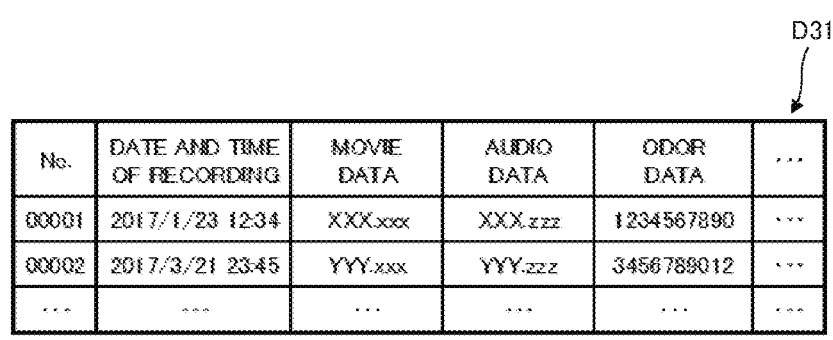
FIG. 23 is a database D31 of Example 3.

FIG. 23 is the database D31 of Example 3. The database D31 stores information about the odor data 305, the audio data 307, and a date and time of recording, etc. in association with the movie data 303 acquired by the movie recording device 313. The database D31 may be stored not only in the storage device 333 but also in a cloud server to which the movie recording terminal 300 is connected via the Internet. When the database D31 is stored in the cloud server, the movie recording terminal 300 may directly store each piece of information stored in the database D31 in the database D31 on the cloud server without storing the information in the storage device 333.

Figure 24:
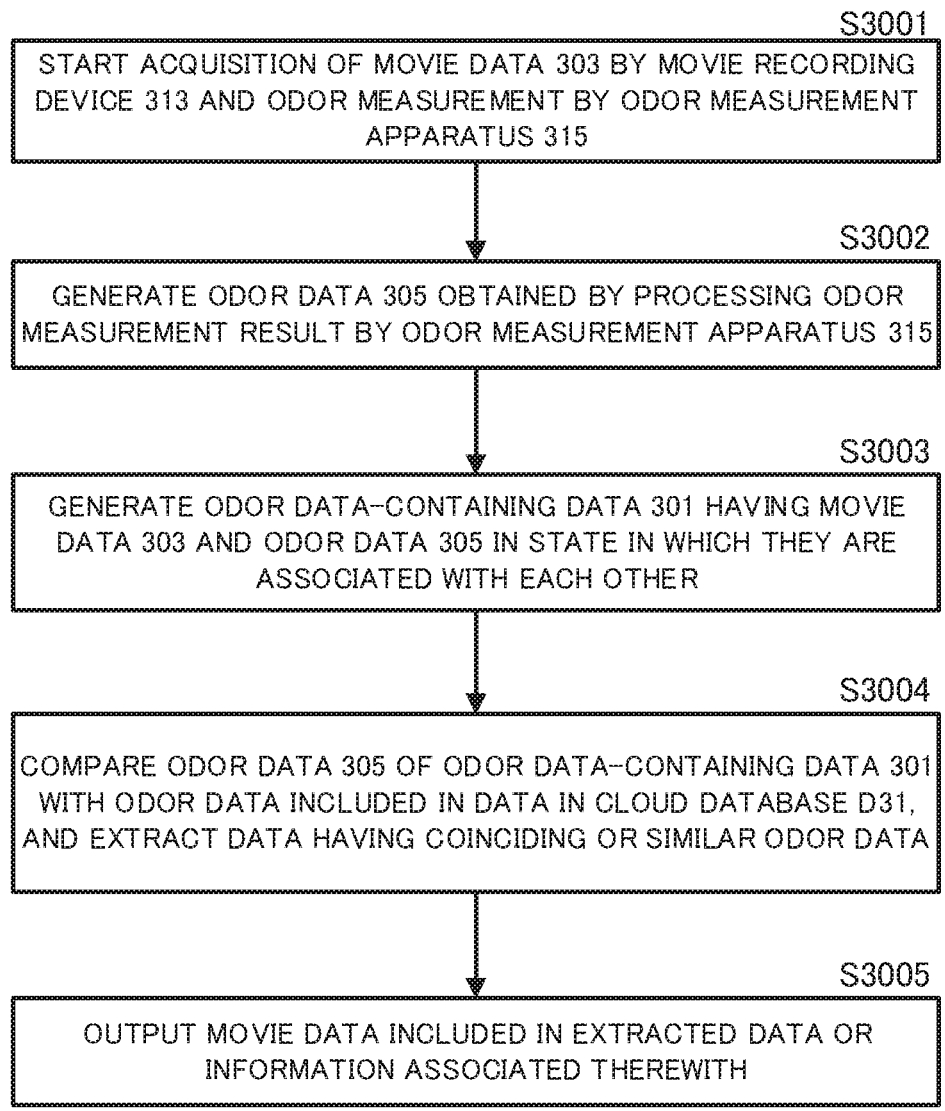
FIG. 24 is a flowchart illustrating processes by the movie recording terminal 300 of Example 3.

Here, a description will be given of a flow of processing of acquisition of the movie data 303, etc. and acquisition of the odor data 305 in the movie recording terminal 300 with reference to FIG. 24. FIG. 24 is a flowchart illustrating processes by the movie recording terminal 300 of Example 3. In step S3001, the movie recording terminal 300 starts acquisition of the movie data 303 by the movie recording device 313, and the odor measurement apparatus 315 starts odor measurement. Specifically, the CPU 331 controls the movie recording device 313 and records the movie data 303. It is preferable that odor measurement by the odor measurement apparatus 315, recording of the movie data 303, and recording of the audio data 307 are simultaneously performed.

In odor measurement by the odor measurement apparatus 315, for example, the odor data 305 may be acquired at a measurement interval of one second. However, when the movie is long, the measurement interval may be increased to 30 seconds, 1 minute, 5 minutes, 10 minutes, 30 minutes, 1 hour, etc. In addition, when it is predicted that there is little change in the odor in the atmospheric air during movie recording, the number of times of odor measurement by the odor measurement apparatus 315 can be reduced. For example, odor measurement may be performed a small number of times in an arbitrary period before start of movie recording, during movie recording, and after end of movie recording.

In S3002, the CPU 331 processes the odor measurement result by the odor measurement apparatus 315 and acquires the odor data 305. Specifically, the CPU 331 acquires the odor measurement result by the odor measurement apparatus 315, calculates a difference thereof, and obtains the odor data 305 as processed data.

In step S3003, the CPU 331 generates odor data-containing data 301 having the movie data 303 and the odor data 305 in a state in which the movie data 303 and the odor data 305 are associated with each other.

In S3004, the CPU 331 compares the odor data 305 of the odor data-containing data 301 with the odor data included in the data in the database D31. Then, in the compared data, data having coinciding or similar odor data is extracted from the database D31. The database D31 may be stored in the storage device 333 or may be stored in a cloud server communicably connected via the Internet. When the database D31 is stored in the cloud server, the CPU 331 can download the extracted data and store the data in the storage device 333.

In S3005, for example, the CPU 331 can output information such as the movie, audio, the date and time of recording, etc. included in the extracted data on a display screen (not illustrated) of the movie recording terminal 300 together with the movie.

(Application 1 of Example 3)

When a movie of a certain dish is captured using the movie recording terminal 300, the odor measurement apparatus 315 of the movie recording terminal 300 measures an odor emitted from the dish, and odor data 305 associated with movie data 303 of the dish is generated. Using the generated odor data 305 as a key, the same or approximate odor data as or to the odor data 305 is retrieved from the database D31, and the same or approximate odor data and information such as movie data associated therewith are extracted from the database D31. In this way, movie data associated with the same or approximate odor data as or to the image-captured dish is obtained.

For example, when a user captures a movie of a favorite dish using the movie recording terminal 300, the user can obtain a cooking video of the dish, a movie of another dish having odor data approximate to the odor data 305 of the dish, etc.

(Application 2 of Example 3)

The movie recording terminal 300 can be used as a security camera, etc. The security camera, etc. is used to photograph an unspecified number of people. There is a great demand for identifying a person on the basis of video from the security camera, etc. Therefore, by using the movie recording terminal 300 as the security camera, etc., the odor measurement apparatus 315 can detect a body odor or a perfume odor emitted by a person who enters an image-capturing range of a movie. When odor data 305 obtained by measuring a body odor of a person to be identified is stored in the database D31, etc., in addition to identifying the person based on the movie, it is possible to identify the person based on the odor data 305 obtained using the movie recording terminal 300. For this reason, in addition to identifying the person based on the movie, it is possible to identify the person based on the odor data 305, and it is expected that accuracy of person identification will be greatly improved.

For example, in the case of searching for a lost child or a criminal, when odor data of the lost child or the criminal can be acquired in advance, the odor data can be stored in the database D31 together with movie data and image data. Further, if the security camera as the movie recording terminal 300 captures an image of the lost child or the criminal, and odor data 305 thereof can be acquired, when the acquired odor data 305 coincides with or approximates to the odor data stored in the database D31, the person can be identified. In this instance, referring to identification of the person, accuracy of person identification is expected to be improved by combining identification of the person based on the movie captured and identification of the person based on the odor data using the movie recording terminal 300.

Even though the preferable embodiment of the invention has been described above, the invention is not limited thereto, and various modifications or changes can be made within a range of a subject matter thereof. For example, the invention includes the following points.

(Point 1) A point is a data structure including a main data storage area in which main data is stored, and an odor data storage area in which odor data based on a measurement result of an odor in an air measured by an odor sensor is stored.

According to this point, it is possible to retrieve and extract data associated with specific odor data from a data set.

(Point 2) The data structure may be characterized in that the main data storage area includes a main data ID area for storing a main data ID indicating that data stored in the main data storage area is the main data, and/or the odor data storage area includes an odor data ID area for storing an odor data ID indicating that data stored in the odor data storage area is the odor data.

(Point 3) In the data structure, the odor data storage area may store a plurality of pieces of the odor data.

(Point 4) In the data structure, the odor data storage area may have a plurality of odor data ID areas.

(Point 5) In the data structure, the odor sensor may include a plurality of sensor elements, each of which includes a substance adsorbing membrane which absorbs an odor substance in the air, and a detector; the substance adsorbing membrane may have a different adsorption characteristic for the odor substance for each of the sensor elements; the plurality of sensor elements may output different measurement results according to an amount of adsorption of the odor substance to the substance adsorbing membrane; and the plurality of pieces of the odor data may be the plurality of sensor elements, respectively.

(Point 6) In the data structure, the odor data may be a measurement result of the odor in the air measured by the odor sensor and is transitional data indicating a temporal change of the odor in the air.

(Point 7) In the data structure, the transitional data may include a plurality of data sets, each of which has a measurement value obtained by measuring the odor in the air using the odor sensor at a predetermined time interval over a predetermined time width and a measurement time of the measurement value.

(Point 8) In the data structure, the odor data may be a measurement result of the odor in the air measured by the odor sensor, and may be difference data between a first measurement result of the odor in the air at a first time or time width and a second measurement result of the odor in the air at a second time or time width for indicating a temporal change of the odor in the air.

(Point 9) In the data structure, the first measurement result may be a measurement result of the odor in the air at the first time, the second measurement result may be a measurement result of the odor in the air at the second time, and a time difference between the first time and the second time may be at least 5 seconds.

(Point 10) In the data structure, the first measurement result may be a maximum value in the measurement result of the odor in the air at the first time width, and the second measurement result may be a minimum value in the measurement result of the odor in the air at the second time width.

(Point 11) In the data structure, the main data may include at least one of image data, movie data, audio data, text data, and location data, and the main data storage area and the odor data storage area may be associated with each other.

(Point 12) A point is a composite data generation device including main data generating means which generates the main data, and the odor sensor, in which composite data based on the data structure according to any one of point 1 to point 11 is generated.

REFERENCE SIGNS LIST

1: odor data-containing data
3: main data
4: main data storage area
5: odor data
6: odor data storage area
7: element data
8: element data storage area
9: element data point
10: odor sensor
11: sensor element
13: substance adsorbing membrane
15: detector
17: sensor substrate
19: sensor surface
23: main data ID
24: main data ID area
25: odor data ID
26: odor data ID area
27: element data ID
28: element data ID area
29: time label
30: time label area
50: odor measurement apparatus
51: arithmetic processing device (CPU) (of odor measurement apparatus)
53: storage device (of odor measurement apparatus)
55: control device
56: introduction port
57: control device
58: ventilation opening
59: control device
60: ventilation opening
100: diagnostic apparatus
101: odor data-containing data
103: image data
105: odor data
111: gantry
112: X-ray irradiation device
113: X-ray detection device
115: odor measurement apparatus
117: bed
131: arithmetic processing device (CPU) (of diagnostic apparatus)
133: storage device (of diagnostic apparatus)
151: arithmetic processing device (CPU) (of odor measurement apparatus)
153: storage device (of odor measurement apparatus)
155$a$: sensor element
155$b$: sensor element
155$c$: sensor element
200: portable information terminal
201: odor data-containing data
203: location data
205: odor data
211: display screen
213: GPS device
215: odor measurement apparatus
217: imaging device
219: atmospheric pressure measurement apparatus
231: arithmetic processing device (CPU) (of portable information terminal)
233: storage device (of portable information terminal)
251: arithmetic processing device (CPU) (of odor measurement apparatus)
253: storage device (of odor measurement apparatus)
255$a$: sensor element
255$b$: sensor element
255$c$: sensor element
300: movie recording terminal
301: odor data-containing data
303: movie data
305: odor data
307: audio data
311: lens 313: movie recording device
315: odor measurement apparatus
317: audio recording device
331: arithmetic processing device (CPU) (of movie recording terminal)
333: storage device (of movie recording terminal)
351: arithmetic processing device (CPU) (of movie recording terminal)
353: storage device (of movie recording terminal)
355a: sensor element
355b: sensor element
355c: sensor element
D1: measurement result database
D2: processed database
D11: database (of Example 1)
D21: database (of Example 2)
D31: database (of Example 3)
P11: program (of Example 1)
P21: program (of Example 2)
P31: program (of Example 3)
Pa: program

What is claimed is:

1. A data structure comprising:
a main data storage area in which main data is stored; and
an odor data storage area in which odor data based on a measurement result of an odor in air measured by an odor sensor is stored,
wherein, during operation of the odor sensor, the measurement result is made continuously and corresponds to a value of a concentration of an odor substance,
wherein the odor data comprises a value of a difference between a maximal value and a first minimal value after the maximal value for the measurement result,
wherein the odor sensor comprises:
a plurality of sensor elements, wherein each of the plurality of sensor elements comprises a substance adsorbing membrane which absorbs an odor substance in the air, and
a detector;
wherein the substance adsorbing membrane has a different adsorption characteristic for the odor substance for each of the sensor elements;
wherein the plurality of sensor elements outputs different measurement results according to an amount of adsorption of the odor substance to the substance adsorbing membrane; and
wherein a plurality of pieces of the odor data corresponds to the plurality of sensor elements, respectively.

2. The data structure according to claim 1, wherein:
the main data storage area comprises a main data ID area for storing a main data ID indicating that data stored in the main data storage area is the main data, and/or
the odor data storage area comprises an odor data ID area for storing an odor data ID indicating that data stored in the odor data storage area is the odor data.

3. The data structure according to claim 2, wherein the odor data storage area stores the plurality of pieces of the odor data.

4. The data structure according to claim 2, wherein the odor data storage area has a plurality of odor data ID areas.

5. The data structure according to claim 2,
wherein the substance adsorbing membrane comprises a thin film with a dopant.

6. The data structure according to claim 2, wherein the odor data is a measurement result of the odor in the air measured by the odor sensor and is transitional data indicating a temporal change of the odor in the air.

7. The data structure according to claim 1, wherein the odor data storage area stores the plurality of pieces of the odor data.

8. The data structure according to claim 7, wherein the odor data is a measurement result of the odor in the air measured by the odor sensor and is transitional data indicating a temporal change of the odor in the air.

9. The data structure according to claim 1, wherein the odor data storage area has a plurality of odor data ID areas.

10. The data structure according to claim 1,
wherein the substance adsorbing membrane comprises a thin film with a dopant.

11. The data structure of claim 10, wherein the thin film is formed of a π electron-conjugated polymer, and wherein the dopant comprises at least one of an inorganic acid, an organic acid, and an ionic liquid.

12. The data structure according to claim 1, wherein the odor data is a measurement result of the odor in the air measured by the odor sensor and is transitional data indicating a temporal change of the odor in the air.

13. The data structure according to claim 12, wherein the transitional data comprises a plurality of data sets, wherein each of the plurality of data sets has a measurement value obtained by measuring the odor in the air using the odor sensor at a predetermined time interval over a predetermined time width and a measurement time of the measurement value.

14. The data structure according to claim 1, wherein the first point in time and the second point in time differ by at least 5 seconds.

15. The data structure according to claim 1, wherein:
the first measurement result is a maximum value in the measurement result of the odor in the air at the first point in time, and
the second measurement result is a minimum value in the measurement result of the odor in the air at the second point in time.

16. The data structure according to claim 1, wherein:
the main data comprises at least one of image data, movie data, audio data, text data, and location data, and
the main data storage area and the odor data storage area are associated with each other.

17. A composite data generation device comprising:
main data generating means which generates the main data; and
the odor sensor,
wherein composite data based on the data structure according to claim 1 is generated.

18. The data structure of claim 1, wherein the main data and the odor data are associated, wherein composite data is generated by the odor sensor, and wherein the composite data comprises a combination of the main data and the odor data.

19. A data structure comprising:
a main data storage area in which main data is stored; and
an odor data storage area in which odor data is stored,
wherein the odor data comprises (i) a plurality of continuous measurements of an odor in air over a predetermined period of time, and (ii) a plurality of difference values between two or more measurements in the plurality of continuous measurements,
wherein the plurality of continuous measurements are made by an odor sensor,
wherein the odor sensor comprises:

a plurality of sensor elements, wherein each of the plurality of sensor elements comprises a substance adsorbing membrane which absorbs an odor substance in the air, and a detector;

wherein the substance adsorbing membrane has a different adsorption characteristic for the odor substance for each of the sensor elements;

wherein the plurality of sensor elements outputs different measurement results according to an amount of adsorption of the odor substance to the substance adsorbing membrane; and wherein a plurality of pieces of the odor data corresponds to the plurality of sensor elements, respectively.

20. A data structure comprising:

a main data storage area in which main data is stored; and an odor data storage area in which odor data based on a measurement result of an odor in air measured by an odor sensor is stored, wherein the odor data comprises a plurality of difference values between measurements of an odor in air over a predetermined period of time, wherein the measurements are made during operation of an odor sensor, wherein the plurality of difference values comprises a difference value between (i) a maximum value during a first period of time in the predetermined period of time, and (ii) a minimum value during the first period of time, wherein the odor sensor comprises:

a plurality of sensor elements, wherein each of the plurality of sensor elements comprises a substance adsorbing membrane which absorbs an odor substance in the air, and a detector;

wherein the substance adsorbing membrane has a different adsorption characteristic for the odor substance for each of the sensor elements;

wherein the plurality of sensor elements outputs different measurement results according to an amount of adsorption of the odor substance to the substance adsorbing membrane; and wherein a plurality of pieces of the odor data corresponds to the plurality of sensor elements, respectively.

* * * * *